United States Patent [19]
Clausen et al.

[11] Patent Number: 5,871,990
[45] Date of Patent: *Feb. 16, 1999

[54] UDP-N-ACETYL-α-D-GALACTOSAMINE: POLYPEPTIDE N-ACETYLGALACTOSAMINYLTRANSFERASE, GALNAC-T3

[76] Inventors: Henrik Clausen, Norske Allé 3, Holte, Denmark, DK-2840; Eric Paul Bennett, Jaegersborgvej 32, Lyngby, Denmark, DK-2800

[*] Notice: This patent issued on a continued prosecution application filed under 37 CFR 1.53(d), and is subject to the twenty year patent term provisions of 35 U.S.C. 154(a)(2).

[21] Appl. No.: 648,298

[22] Filed: May 15, 1996

[51] Int. Cl.$^6$ ............... C12N 9/10; C12N 1/20; C12P 21/06; C07H 21/04
[52] U.S. Cl. ............. 435/193; 435/69.1; 435/252.3; 435/320.1; 435/6; 536/23.2; 536/24.3; 536/24.31; 530/350
[58] Field of Search ............... 435/193, 69.1, 435/252.3, 320.1, 6; 536/23.1, 24.3; 530/350

[56] References Cited

U.S. PATENT DOCUMENTS 5,177,015  1/1993  Matsuura et al. ............. 435/193

FOREIGN PATENT DOCUMENTS

0364652 A2  2/1990  European Pat. Off. .
9426906 A3  11/1994  WIPO .

OTHER PUBLICATIONS

Clausen, et al., *Complex Carbohydrates in Drug Research, Alfred Benzon Symposium*, "Simple mucin type O–glycans of HIV: Enzymatic prediction of glycosylation sites for vaccine construction," 36:297–315, 1994.
Sorensen, et al., *J. Biol. Chem.*, UDP–N–acetyl–α–D–galactosamine:polypeptide N–Acetylgalactosaminyltransferase, 270(41):24166–24173, 1995.
White, et al., *J. Biol. Chem.*, Purification and cDNA and Cloning of a Human UDP–N–acetyl–β–D–galatosamine:polypeptide N–Acetylgalatosaminyltransferase, 270(41):24156–24165, 1995.
Matsuura, et al., *J. Biol. Chem.*, "An α–N–Acetylgalactosaminylation at the Threonine Residue of a Defined Peptide Sequence Creates the Oncofetal Peptide Epitope in Human Fibronectin," 264(18):10472–10476, 1989.
Matsuura, et al., *J. Biol. Chem.*, "The Oncofetal Structure of Human Fibronectin Defined by Monoclonal Antibody FDC–6," 263(7):3314–3322, 1988.
Hagen, et al., *J. Biol. Chem.*, Purification, Cloning, and Expression of a Bovine UDP–GalNAc: Polypeptide N–Acetylgalactosaminyltransferase, 268(25):18960–18965, 1993.
Homa, et al., *J. Biol. Chem.*, Isolation and Expression of a cDNA Clone Encoding a Bovine UDP–GalNAc: Polypeptide N–Acetylgalactosaminyltransferase, 268(17), pp. 12609–12616, 1993.
Grunnet, et al., *Vox Sang.*, "Evaluation of Histo–Blood Group ABO Genotyping in a Danish Population: Frequency of a Novel O Allele Defined as $O^2$," 67:210–215, 1994.
Luo, et al., *Am. J. Hum. Genet.*, "Affected–Sib–Pair Mapping of a Novel Susceptibility Gene to Insulin–Dependent Diabetes Mellitus (IDDM8) on Chromosome 6q25–q27," 57:911–919, 1995.
Copeman, et al.,*Nature Genetics*, Linkage disequilibrium mapping of a type 1 diabetes susceptibility gene (IDDM7) to chromosome 2q31–q33, 9:80–85, 1995.
Goodfellow, et al., *Nature*, "From the simple to the complex," 371:104–105, 1994.
Bennett, et al., *Biochem. and Biophys. Res. Comm.*, "Genomic Cloning of the Human Histo–Blood Group ABO Locus," 206(1):318–325, 1995.
EMBL, Database GenBank/DDBJ, accession No., X92689, Sequence HSGNT3, Apr. 30, 1996, Bennett, E.P. et al.
Bennett, E.P. et al., *J. Biol. Chem.* 271:17006–17012, Jul. 19, 1996.

*Primary Examiner*—Charles L. Patterson, Jr.
*Assistant Examiner*—Tekchand Saidha
*Attorney, Agent, or Firm*—Darby & Darby

[57] ABSTRACT

A novel gene defining a novel enzyme in the UDP-N-acetyl-α-D-galactosamine: polypeptide N-acetylgalactosaminyltransferase family, termed GalNAc-T3, with unique enzymatic properties is disclosed. The enzymatic activity of GalNAc-T3 is shown to be distinct from that of two previously identified enzymes of this gene family. The invention discloses isolated DNA molecules and DNA constructs encoding GalNAc-T3 and derivatives thereof by way of amino acid deletion, substitution or insertion exhibiting GalNAc-T3 activity, as well as cloning and expression vectors including such DNA, cells transfected with the vectors, and recombinant methods for providing GalNAc-T3. The enzyme GalNAc-T3 and GalNAc-T3-active derivatives thereof are disclosed, in particular soluble derivatives comprising the catalytically active domain of GalNAc-T3. Further, the invention discloses methods of obtaining N-acetylgalactosamine glycosylated peptides or proteins by use of an enzymically active GalNAc-T3 protein or fusion protein thereof or by using cells stably transfected with a vector including DNA encoding an enzymatically active GalNAc-T3 protein as an expression system for recombinant production of such glycopeptides or glycoproteins. Also a method for the production of a vaccine by modifying the O-glycosylation pattern of an eukaryotic cell, and a method for the identification of DNA sequence variations in the GalNAc-T3 gene by isolating DNA from a patient, amplifying GalNAc-T3-coding exons by PCR, and detecting the presence of DNA sequence variation, are disclosed.

28 Claims, 11 Drawing Sheets

FIG. 1

Polypeptide GalNAc-Transferase Motif

C. Elegans

**********V*M**S*HPR*********Q*******AKV*HH*AA*T*******

GalNAc-T1

$^{316}$WGGENLEISFRIWQCGGTLEIVTCSHVGHVFRKATPYTFPGGTGQIINKNNRRLAEVWMDE$^{376}$
$^{331}$********V**S*IPR***QH****S*TVFAR*TA*****$^{391}$

GalNAc-T2

$^{387}$*****I*M**V***QMPV******SKS*HS**K*-*V*AR*QA**********$^{446}$

GalNAc-T3

---

5'********T****TTGGAG$^{982}$ ———————————— C. Elegans ———————————— $^{128}$****T****C*3'

| Primer EBHC100 | | | | | | Primer EBHC106 | | | | |
|---|---|---|---|---|---|---|---|---|---|---|
| W | G | G | E | N | L | E | A | E | V | W | M | D |

5'TGGGGAGGAGARAACCTAGA$^{965}$ ———— GalNAc-T1 ———— AGAAGTATGGATGGATGAAT$^{3'}$
5'TGGGGAGGAGAAAACCTAGA$^{1010}$ ———— GalNAc-T2 ———— $^{1110}$AGAAGTGTGGATGGATGAAT$^{3'}$
5'********G*****$^{1178}$ ———— GalNAc-T3 ———— $^{1155}$*GC***********$^{3'}$

5'********T**TA$^{1178}$ ———— GalNAc-T3 ———— $^{1320}$*******C*******$^{3'}$

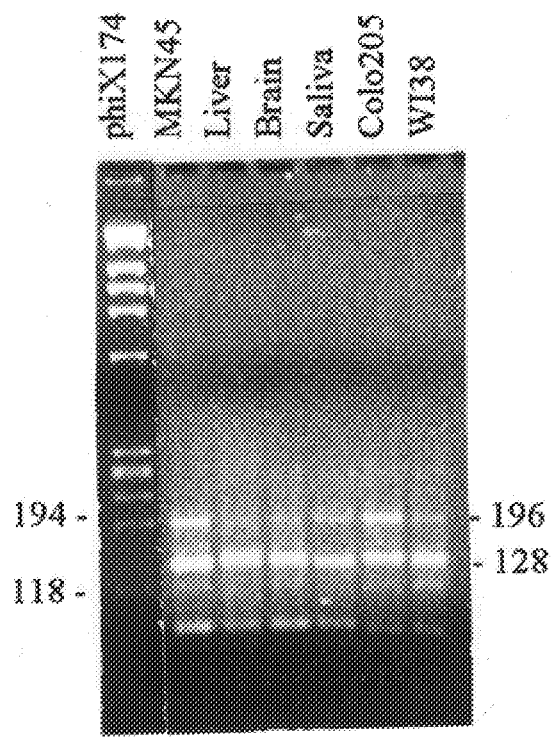
FIG. 2
FIG. 7
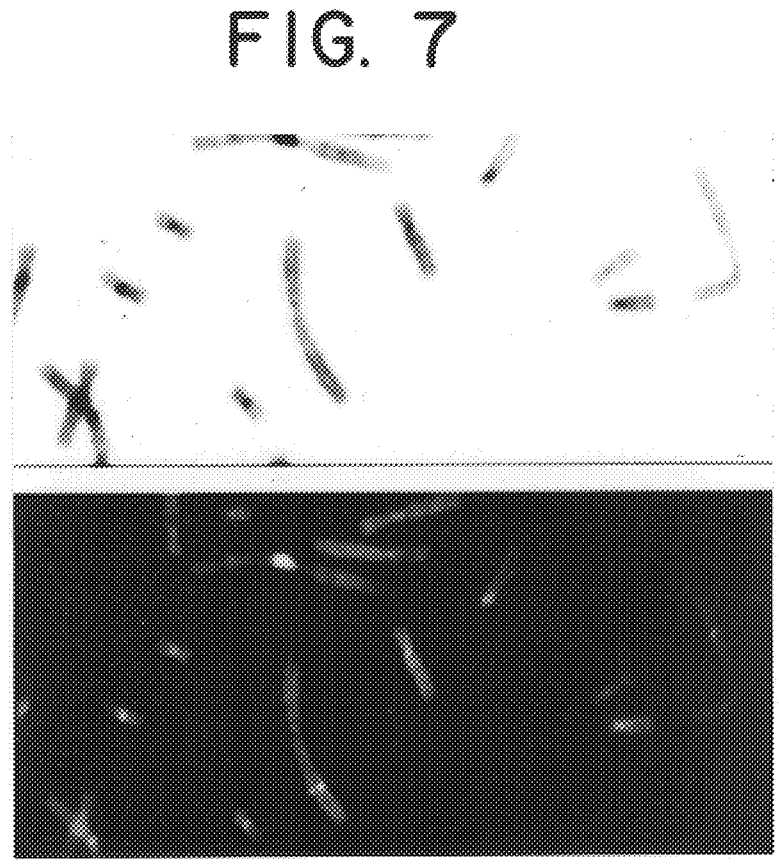

FIG. 3A

```
 -990   ..........................................
 -900   TAAACTTGCTGTCCTGTTCTTAGGGTCGATTGCAAGCAATATTTTA
 -750   GCTGTGAGCTATTAAAACTAGCTGTTATATAACAACAAATTAAATG
 -600   TATCATTCATTAAGCTGGAGCAGATCACAGTTTGAGGGTAAACTAC
 -450   TTTGATTCCTTGGTTATCAAGTGAAGATATTCTTTTTAACTCAAA
 -300   ATAAATTGTAGTAAATTGTAACAATTATTTCTTCCAAAAGTGTAA
 -150   GGACTGAATAGCTACTAATACCATCGATCATTTCTGTTTATAGGTA

1      M  A  H  L  K  R  L  V  K  L  H  I  K  R  H
    1   ATGGCTCACCTAAAGCGACTAGTAAAATTACACATTAAAAGACATT

51      R  M  E  R  N  M  K  N  K  N  K  M  L  D  L
  151   AGGATGGAAAGGAACATGAAAAACAAAAACAAGATGTTGGATTTAA

101      Y  Y  T  A  A  E  L  K  P  V  L  D  R  P  P
  301   TATTATACAGCAGCAGAATTGAAGCCTGTCCTTGACCGTCCACCTC

151      N  A  F  A  S  D  R  I  S  L  H  R  D  L  G
  451   AATGCTTTCGCAAGTGACAGGATTTCTTTGCACCGAGATCTTGGAC

201      L  L  R  T  V  H  S  V  L  Y  S  S  P  A  I
  601   TTGCTTAGAACTGTCCACAGTGTGCTCTATTCTTCACCTGCAATAC

251      Q  R  E  R  K  G  L  I  T  A  R  L  L  G  A
  751   CAAAGAGAAAGAAAAGGTCTGATCACTGCTCGGTTGCTAGGAGCAA

301      V  V  S  P  D  I  A  S  I  D  L  N  T  F  E
  901   GTCGTAAGTCCAGATATTGCATCCATAGATCTGAACACGTTTGAAT

351      K  D  E  T  Y  P  I  K  T  P  T  F  A  G  G
 1051   AAAGATGAAACCTACCCAATTAAAACACCCACTTTTGCAGGAGGAC

401      C  G  G  Q  L  E  I  M  P  C  S  V  V  G  H
 1201   TGTGGTGGGCAGTTGGAGATTATGCCTTGCTCTGTTGTTGGACATG

451      F  Y  R  R  N  T  D  A  A  K  I  V  K  Q  K
 1351   TTTTATAGGAGAAATACAGATGCAGCAAAAATTGTTAAACAAAAAG

501      L  N  P  V  I  S  G  Y  I  K  S  V  G  Q  P
 1501   CTTAATCCTGTTATATCTGGATACATTAAAAGCGTTGGTCAGCCTC

551      E  I  R  H  N  I  Q  K  E  L  C  L  H  A  A
 1651   GAAATTCGGCACAACATCCAGAAGGAATTATGTCTTCATGCTGCTC

601      F  L  K  M  C  L  S  A  N  G  E  H  P  S  L
 1801   TTCTTAAAAATGTGCCTTTCAGCAAATGGAGAGCATCCAAGTTTAG

1951   CTGTGACTAGGCATACACTGTAGTTTTTGAAAATTATGCAAAAGCA
 2101   ATACCAAAGACTATTTCAAAATGTCCAGATGTAGGGAAGAGATGT
 2251   TATTTCCCCTAGTTTTTGGGGGGATAGGAAGAAAGATTTGTTACT
 2401   GGTGAACTTTTTTTGCGTTTGGTTTACTTGTCTGTCAAATGTTTC
 2551   TAAGTCTTCCTTAAATGACTTTTCTTAAGTAATGATACTGTGTGTT
 2701   TGAATGTTTGTGATATTAAATTTCAAATGCAGAATACTTGACTCAT
 2851   AACACAATAAAAAATCCTCAACACTAAAAAAAAAAAAA
```

FIG. 3B

```
                  TGGCTATCGCGGCTCATAGTATGTAATCGTTTCCTAAGAAGTCCG
TCAAACCAAATTCTGCTTTTTTAACTTTATGACTTGTATAGGCTCCGTACAGACACTTC
CTGTTGATTTTCTTGTTTTTAGGGGTTCCTTCAGGAGTCACAAGTACTATTGGGTTGGA
ATAAAATGAAGGCCACTATTTTAGATGGATGCCTGATAGTACTTATCAGTATACCCTTA
ATATATTTATAAAATTAATTTTATACATAGTATATAGTGGATATTAGAGTTTAAAAAGA
TTTTCTTGAGGACAAGATATCTTTGTATTCTCATTAACCATAAGAGTACATTGGTAGCT
CTACCATAAAGATACCTTCTTCTCAGCAAATCTATGATAAAAAATATAAGTAACAGAAG
```

```
  Y  H  K  K  F  W  K  L  G  A  V  I  F  F  F  I  I  V  L  V
           ACCATAAAAAGTTCTGGAAGCTTGGTGCAGTAATTTTTTCTTTATAATAGTTTGGTT

M  L  E  A  V  N  N  I  K  D  A  M  P  K  M  Q  I  G  A  P
  TGCTAGAAGCTGTAAACAATATTAAGGATGCCATGCCAAAAATGCAAATAGGAGCACCT

Q  D  S  N  A  P  G  A  S  G  K  A  F  K  T  T  N* L  S  V
  AGGATTCAAATGCACCTGGTGCTTCTGGTAAAGCATTCAAGACAACCAATTTAAGTGTT

P  D  T  R  P  P  E  C  I  E  Q  K  F  K  R  C  P  P  L  P
  CAGACACTCGACCTCCTGAATGTATTGAACAAAAATTTAAGCGCTGCCCTCCCCTGCCC

L  L  K  E  I  I  L  V  D  D  A  S  V  D  E  Y  L  H  D  K
  TGCTGAAGGAAATCATTTTGGTGGATGATGCTAGTGTAGATGAGTACTTACATGATAAA

T  V  A  T  A  E  T  L  T  F  L  D  A  H  C  E  C  F  Y  G
  CAGTCGCAACAGCTGAAACGCTCACATTTTTAGATGCTCACTGTGAGTGTTTCTATGGT

F  N  K  P  S  P  Y  G  S  N  H  N  R  G  N  F  D  W  S  L
  TCAACAAACCTTCTCCTTATGGAAGTAACCATAACCGTGGAAATTTTGACTGGAGTCTT

L  F  S  I  S  K  E  Y  F  E  Y  I  G  S  Y  D  E  E  M  E
  TTTTTTCCATATCAAAAGAATATTTTGAGTATATTGGAAGCTATGATGAAGAAATGGAA

V  F  R  S  K  S  P  H  S  F  P  K  G  T  Q  V  I  A  R  N
  TTTTTCGCAGCAAAAGCCCTCATAGCTTTCCAAAAGGCACTCAGGTGATTGCTAGAAAC

A  F  G  D  L  S  K  R  F  E  I  K  H  R  L  R  C  K  N* F
  CATTTGGTGATCTTTCAAAAGATTTGAAATAAAACACCGTCTTCGGTGTAAAAATTTT

L  C  L  D  V  G  E  N  N  Q  G  G  K  P  L  I  M  Y  T  C
  TATGTCTGGATGTTGGAGAAAACAATCAAGGAGGCAAACCATTAATTATGTATACATGT

Q  G  L  V  Q  L  K  A  C  T  Y  K  G  H  K  T  V  V  T  G
  AAGGTCTCGTTCAGCTGAAGGCATGTACCTACAAAGGTCACAAGACAGTTGTCACTGGA

V  S  C  N* P  S  D  P  L  Q  K  W  I  L  S  Q  N  D  *
  TGTCATGCAACCCATCAGATCCACTCCAAAAATGGATACTTAGCCAAAATGATTAAGTG
```

```
GCTAAATGTAACTTATTCCAAGTGCATTTTTCTTATTTATATCTTTATGTAGCACTATC
TTACAGTATGATGAAAATAATTTTCCAAGTAAAGTGAAGTTTGTGTGTTTTGTACACTT
GTATTTTTTAACTACATAAAAATAGATCAATAAATGTCAGCATTGGCCTCTGTGTACA
CTTAAACATGAAACTGAATAAGGAGAAGAGTATTTTAACACTTAAATTTCTTGGCAAA
TTCCCAAAGCACTTTTAAAAAAATTTTTATAAATTACTATCTGTTGAAAAGGTGTCCTT
TTAAAGCTAAATTTTGTTACTGATTCAATTATAATTGTAATGGATTTTTGACTTTGTAA
```

FIG. 3C

```
                                                              -901
TATTTTTCTTTTCCTTTGCTCCTGTTGTCCCATATTAGGGTTTAA                 -751
AAGTAAAGCTAATGAATTCTCTTTTTACTATTAGATCTTGTATTT                 -601
AAATCTGGGAGAATAATAGTTTACTTACTGATGAAACTGCTGTAT                 -451
CTTCCTTATGGAGCTCTCTTTTTTGTAATTTATTTAATGAGGTCC                 -301
ATGTATTTTTAATGGAGAGGAATATCAATATTTTTGCAACCCCA                  -151
TATGTTCAGTTGTTGGTTAAATGAATGAATTGAGCCATGCCTGTA                 -1
AAGAAATAACTGTTATTTGTCAAGTGACAAGCTTTTAATGTCAGA

L  M  Q  R  E  V  S  V  Q  Y  S  K  E  E  S               50
TTAATGCAAAGAGAAGTAAGTGTTCAATATTCCAAAGAGGAATCA                 150

V  R  Q  N  I  D  A  G  E  R  P  C  L  Q  G               100
GTCAGGCAAAACATTGATGCTGGTGAGAGACCTTGTTTGCAAGGA                 300

E  E  Q  K  E  K  E  R  G  E  A  K  H  C  F               150
GAAGAGCAAAAGGAAAAGGAACGTGGGGAAGCTAAACACTGCTTT                 450

T  T  S  V  I  I  V  F  H  N  E  A  W  S  T               200
ACCACCAGTGTCATAATAGTTTTTCATAATGAAGCGTGGTCCACG                 600

L  D  E  Y  V  K  Q  F  S  I  V  K  I  V  R               250
CTAGATGAATATGTAAAACAATTTTCTATAGTAAAAATAGTCAGA                 750

W  L  E  P  L  L  A  R  I  A  E  N* Y  T  A               300
TGGCTAGAACCTCTGTTGGCCAGAATAGCTGAGAACTACACGGCT                 900

S  F  G  W  E  S  L  P  D  H  E  K  Q  R  R               350
TCATTTGGCTGGGAGTCGCTTCCTGATCATGAGAAGCAAAGAAGG                 1050

I  W  G  G  E  N  I  E  M  S  F  R  V  W  Q               400
ATCTGGGGAGGTGAAAATATAGAAATGTCTTTCAGAGTATGGCAA                 1200

Q  V  R  L  A  E  V  W  M  D  E  Y  K  E  I               450
CAAGTTCGCCTTGCAGAAGTCTGGATGGATGAATACAAGGAAATA                 1350

T  W  Y  L  N  N  I  Y  P  E  V  Y  V  P  D               500
ACATGGTATCTGAACAACATTTATCCAGAGGTGTATGTGCCAGAC                 1500

H  G  L  G  G  N  Q  Y  F  E  Y  S  A  Q  H               550
CATGGACTTGGGGGAAACCAGTACTTTGAATACTCTGCTCAACAT                 1650

E  Q  I  W  E  I  Q  K  D  Q  L  L  Y  N  P               600
GAGCAGATATGGGAGATCCAGAAGGATCAACTTCTATACAATCCA                 1800

633
TTCCTTAAAATTAAGTTGAAAAAGGAAATATTCTTTCTCATAAAA                 1950

TACAGAAATTCTGCAAGTTTCTGTTTCAAAGCACAATAACTAGTA                 2100
AGGGATATATATATATATAGCTACATTCACACACTCACAATTTAAAA               2250
AACCAAGAGCTTTTACAGATCCAGAATTTATTAGTTTAAAATGCA                 2400
TTTTAAAACATTTTTTAGTCTGTAATACACTCCACTTGAAGCACT                 2550
TTCCTTTCTTCTAGTATTTTTTTCTTACCAAAATTCACTAATCT                  2700
TGGATTCTTTTCATCAAAAAGCCTTATTTTTTTATCTATGTGGAA                 2850
```

FIG. 4A

```
                 A                                                                                      A
         MR-----KFAYCKVLATSLIWVLLDMFLLYES------ECN--KCDEK-----KERGLPAGDVLEPVQK
T1   ::RRS------RML:CFAFL:::G----IA:YMYSGGG---------SA:AG:---------
T2   :AHLKRLVKLHI::RHYHKKE-:K:GAVIFFFIVLVLMQR:VSVQYSK:ESRMERNMK-NKNKM:DLMLE
T3   :LSVGGGRS:V:RA:I:::IV:L:I:VVI:F:YLDPSTSQQQP--FPEDNRILNRA:-----------
Ce

T1    82  NQFNLMASEMIALNRSL-PDVRLEGCKT---KVYPDNLPTTSVVIFHNEAWSTLLRTVHSVINRSPRHM
T2   102  :K::QVE:DKLRMD:AI-::T:HDQ♦Q----R:QWRVD::A:::::T:::::R:A:::::V::LKK::P:L
T3   148  HC::AF::DR:S:H:D:G::T:PPE♦--IEQKFKRCPP::T:::::I::::::::::::::LYS::AIL
Ce   133  ::::VV:::::SV::T-L::Y:SDA♦R:SGNNLKTAGM:K::II:::::::T:::::L::::::::::L

T1        HDRRTVVCPIIDVISDDTFEYMA------GSDMTYGGENWKLNFRW-YPVPQREMDRRKGDRTLPVRTPTMA
T2        E::TR::S:::::NM:N:Q:VGAS---A:LK-:::::NLV:K:D:MT:E-QRRS:Q:NPVA:IK::MI:
T3        ENYTA::S:D:AS:DLN::::FNKPSPY::NHNR:N:::SLS:G:E-SL:DH:KQ:::DE-:Y:IK:::F:
Ce        E::KR::A:::::::::::VTASET----:W:::N:H:::::-:A::K::LN::GS::SM:IQ:::I:

T1        WMDEEKNFFYIISPGVTKV-----DYGDISSRVGLRHKLQCKPFSWYLENIYPDSQIPRHY-FSLGEIRNV
T2        :::::Y::::Y:AAV:S---ARNVP::NIQ::LE::K::S♦:::K::::VY:ELRV:D:QDIAF:ALQQ-
T3        :::::Y:EI::RRNTDAA:IVKQKAF::L:K:FEIK:R:R♦::N:T:::N::::EVYV:DLNPVIS:Y:KSV
Ce        :::Y:AF::KMV:A----ARNVEA::V:E:KK::ET::♦:S:K:::::::::EAPL:ADER-::A:V:R

T1        LWEYDPVKLTLQHVNSNQCLDKATEEDSQVPSIRDCN-GSRSQQWLLRNVTLPEIF*          559
T2        K::QIEGNSK:R::G::L♦:::SR:AKSGGL-:VEV♦G-PAL::::KFT-LN:QQ*--         571
T3        I::IQKDQ:-:YNPELKM♦:SA----:NGEH::LVS♦:PSDPL:K:I:SQND*----          633
Ce        VEVF:DQAG:::L:KKTGK♦VT----GAD:RVTLDE♦GL:RKD:M:Q:EGYQS:*---         612
```

FIG. 4B

```
PHE----------------------------------------GPG----EMGKPVVIPKEDQEKMKEMFKI
--------------AGGGAGRKEDWNEIDPIKKKDLHHSNGEEKAQSMETLPPGKVRW:DFNQ:AYVGGTMVRSG:DP----YAR
AVNNIKDAMPKMQIGA-PVRQNIDAGERPCLQGYYTAAELKPVLDRPPQDSNA:GASGKAF:TTNLSV:E:KEKERGEAK
---RIEPLPPAAQHDSDPDAHPIQPEKQEKQVYPVDKETANQLRKLMETQAF:::YHGQG:TG:TV:EDKKTIKEKR:LE

IEEIVLVDDASERDFLKRPLESYVKLKVPVHVIRMEQRSGLIRARLKGAAVSKGQVITFLDAHCECTVGWLEPLLARIK
::KE:I::::------YSND:EDGALLGKIEK:R:L:NDR:E::M:SRVR::DAAQAK:L:::::S:::♦:NEH::::::ERVA
LKE:I::::::::VDEY:HDK:DE:::QFSI-:KIV:QRE:K:::T:::L::T:ATAETL::::::::::♦FY::::::::::A
L:E:I::::K:D::Y:VK::D::I:MFPI:LVHL:N::::::::I:T:SEMA:G:ILL:::::V:V:D::::VS:VA

GGLFSIDRDYFQEIGTYDAGMDIWGGENLEISFRIWQCGGTLEIVTCSHVGHVFRKATPYTFPGGTGQIINKNNRRLAEV
::::VM:KF::E:L:K::MM::V::::::::::::::V::::S::::IP♦:R::::::QH::::::S:TVFAR:T::A:::
::::::SKE::EY::S::EE:E::::::I:M:::V::::♦::Q:::MP♦:V:::::SKS:HS::K::-:V:AR:QV:::::
::::A::KQF:YD::S::E::QV::::::::V:M::::S:::HP♦:R::::::::Q:::::::::::AKV:HH:AA:T:::

ETNQCLDNMARKENEKVGI-FNCHGMGGNQVESYTANKEIRTD----DLCL----DVSKLNGPVTMLKC--------H--HLKGNQ
-GTN♦::TLGHFADGV::V-YE♦:NA:::EWAL:KE:SVK----HM:♦:TVV:RAP-GSLIKLQG♦REND------SR:
GQPL♦::VGENNQGG:PL:MYT♦:::L::::Y:E:S:QH::HNIQKE:♦:HAAQ---:L:QLKA♦TYKG:KTVVT:E:
F:EK♦V:TNGK:DGQAP::Q-A♦::A::::AW:L:GKG::---RSD:::♦:SSGH:YQIGSELKLER♦SVSKINV----KH
```

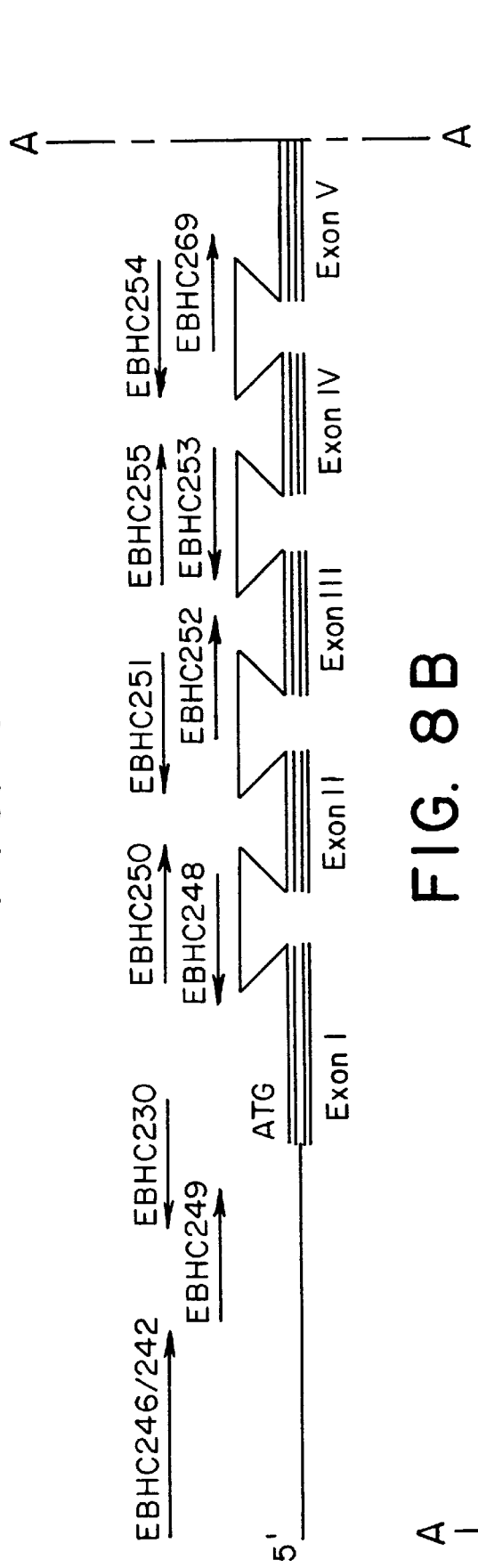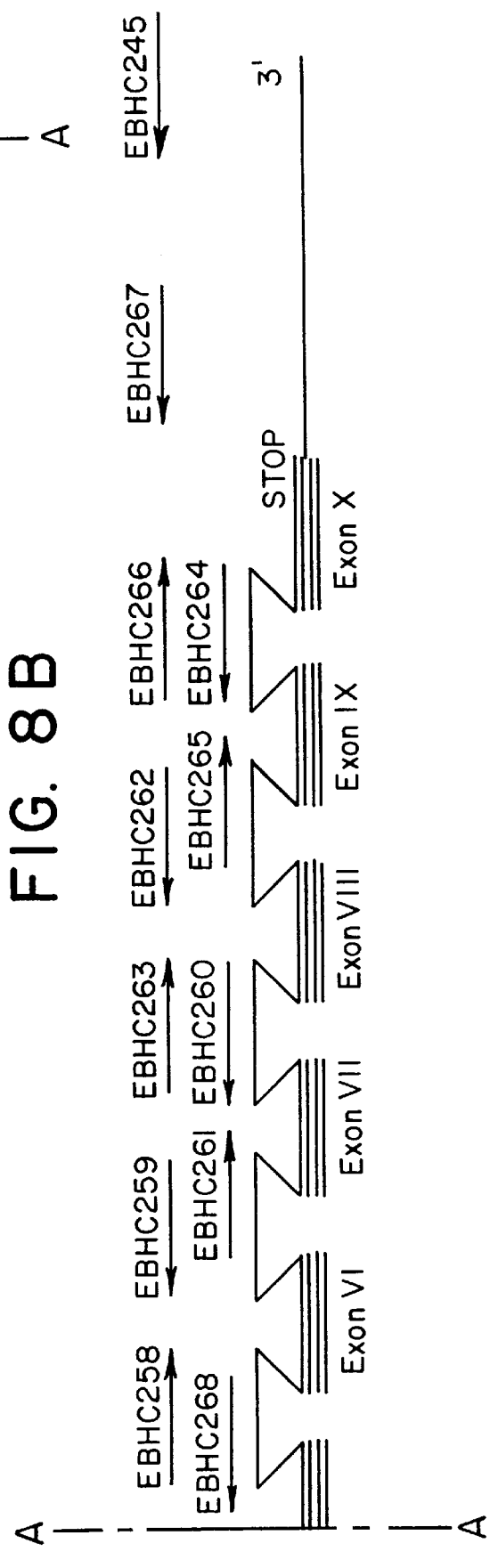
FIG. 8A
FIG. 8B

FIG. 8C

| | | |
|---|---|---|
| EBHC246: | 5'-AGCGGATCCAATCGTTTCCTAAGAAGTCCG | |
| EBHC242: | 5'-AGCGGATCCCTTTATGACTTGTATAGGCTCC | |
| | AGCGGATCCATAGATTTGCTGAGAAGAAGG-3' : | EBHC230 |
| EBHC249: | 5'-AGCGGATCCTGAATAGCTACTAATACCATCG | |
| | AGCGGATCCTGTGATAAAGAATAAACA-3' : | EBHC248 |
| EBHC250: | 5'-AGCGGATCCTTAGCAATGGTATAGCTGTG | |
| | AGCGGATCCACAATACGGATTGGGAAAC-3' : | EBHC251 |
| EBHC252: | 5'-AGCGGATCCTGTGGTTTTCATTGCTTTC | |
| | AGCGGATCCGGAGGGAAAATGTTACAACC-3' : | EBHC253 |
| EBHC255: | 5'-AGCGGATCCTAATTAAAATTCTGTTCCCTC | |
| | AGCGGATCCATTAACCTCAGAGGCAATTGC-3' : | EBHC254 |
| EBHC269: | 5'-AGCGGATCCAAGCTTTGAAAATGTGATATG | |
| | AGCGGATCCTGCTATATTTGATTCCATAGAC-3' : | EBHC268 |
| EBHC258: | 5'-AGCGGATCCGGTGAACTTAAAAGCAACAC | |
| | AGCGGATCCATGCAATTAACTACTTAGC-3' : | EBHC259 |
| EBHC261: | 5'-AGCGGATCCGCATTCCCTTCATTCTCATG | |
| | AGCGGATCCATAAAGGTTGGTGGCAAGGAG-3' : | EBHC260 |
| EBHC263: | 5'-AGCGGATCCTCACATGGATTAAAAACTTTC | |
| | AGCGGATCCATCTCACTTGTGCTTGTAAATGC-3' : | EBHC262 |
| EBHC265: | 5'-AGCGGATCCACATGGGTTGCTTTTGTCAG | |
| | AGCGGATCCCAGATAAGCAAGTAGAGC-3' : | EBHC264 |
| EBHC266: | 5'-AGCGGATCCTGTCACTTAACTATGAGTCTTGG | |
| | AGCGGATCCTAAGTTACATTAGCTGCTTTGC-3' : | EBHC267 |
| | AGCGGATCCGCTTTTTGATGAAAAGAATCCATTAC-3' : | EBHC245 |

:::::::::::::::::::::::::::::::

UDP-N-ACETYL-α-D-GALACTOSAMINE: POLYPEPTIDE N-ACETYLGALACTOSAMINYLTRANSFERASE, GALNAC-T3

TECHNICAL FIELD

The present invention relates generally to the posttranslational modification of proteins termed protein glycosylation, where glycan moieties are added covalently to specific amino acids of proteins. This invention is more particularly related to a family of nucleic acids encoding UDP-N-acetyl-α-D-galactosamine:polypeptide N-acetylgalactosaminyl-transferases (GalNAc-transferases), which initiate O-glycosylation of specific serine and threonine amino acids in proteins by adding N-acetylgalactosamine to the hydroxy group of these amino acids. This invention is more particularly related to a gene encoding the third member of the family of GalNAc-transferases, termed GalNAc-T3, probes to the DNA encoding GalNAc-T3, DNA constructs comprising DNA encoding GalNAc-T3, recombinant plasmids and recombinant methods for producing GalNAc-T3, recombinant methods for stably transfecting cells for expression of GalNAc-T3, and methods for identification of DNA polymorphism in patients.

BACKGROUND OF THE INVENTION

Enzymatic protein glycosylation involves an initiation stage in which glycosyltransferases catalyze the addition of a monosaccharide, or, in the case of asparagine N-linked glycosylation, a preformed oligosaccharide, to an amino acid residue in a given protein. The initiation step of protein glycosylation may be considered the key controlling event leading to the formation of a given glycopeptide linkage (glycoconjugate type), and it involves the essential recognition events between protein and glycosyltransferase which determine the specific sites of glycan attachment. Processing of glycan chains involves the cooperative action of part of the estimated hundreds of different glycosyltransferases successively adding a monosaccharide to the growing glycan chain. Identification and characterization of glycan structures of glycoproteins as well as the specific sites of glycan attachment are important for understanding the structure of a given glycoprotein, its function, and its immunobiology.

The glycosylation of serine and threonine residues during mucin-type O-linked protein glycosylation is catalyzed by a family of polypeptide GalNAc-transferases (EC 2.4.1.41). Two distinct human GalNAc-transferase genes, GalNAc-T1 and -T2, have previously been cloned and characterized (Homa et al. 1993; Hagen et al. 1993; White et al. 1995). In preliminary studies the specificity of recombinant GalNAc-T1 and -T2 with respect to polypeptide acceptors (i.e., acceptor substrates) has been analyzed. Comparison of the total acceptor substrate specificity of recombinant GalNAc-T1 and -T2 with the substrate specificities previously described in extracts of various organs showed that several peptides served as substrates only for galactosyltransferase enzymes present in the organ extracts (Sorensen et al. 1995).

Matsuura et al (1988) reported a tumor-associated de novo O-glycosylation of fibronectin in the IIICS region with the peptide sequence VTHPGY SEQ IN NO:3. In a more recent study Matsuura et al (1989) reported that O-glycosylation of this epitope was only achieved by transferase-containing extracts from fetal tissue or tumor tissue and not normal tissue. Recombinant GalNAc-T1 and GalNAc-T2 have not been found to catalyze O-glycosylation of this peptide sequence.

A peptide derived from the Human Immunodeficiency Virus (HIV$_{IIIB}$) gp120 (GRAFVTIGKIG SEQ ID NO:4) was found to be an effective acceptor substrate for crude GalNAc-transferase extracts from several organs (Sorensen et al. 1995). However, purified GalNAc-T2 (Clausen et al. 1994; Sorensen et al. 1995) and recombinant GalNAc-T1 and GalNAc-T2 did not catalyze glycosylation of this substrate. These implicate additional GalNAc-transferases.

Families of glycosyltransferases with related but distinct acceptor and/or donor substrate specificities may be encoded by homologous genes showing segments of sequence similarity (Schachter, 1994; Kleene et al., 1993). The human GalNAc-transferases T1 and T2 share a segment of 61 amino acids with 82% sequence similarity and this segment is also found in a homologous gene from C. elegans (White et al. 1995, EMBL accession # L16621).

At present, knowledge of the key controlling event of initiation of O-glycosylation of proteins is limited to the involvement of two GalNAc-transferase genes, GalNAc-T1 and GalNAc-T2, and their encoded enzymes. The action of the two hitherto identified enzymes does not account for all observed O-glycosylation, with fibronectin and HIV being notable examples of O-glycosylation not mediated by said enzymes. Access to additional existing GalNAc-transferase genes would allow production of enzymes capable of performing such O-glycosylation initiation. Such enzymes could be used, for example, in pharmaceutical or other commercial applications that require synthetic O-glycosylation of these or other substrates that are not acted upon by GalNAc-T1 or -T2, in order to produce glycosylated polypeptides having particular enzymatic, immuogenic, or other biological and/or physical properties.

Consequently, there exists a need in the art for additional UDP-N-acetyl-α-D-galactosamine: polypeptide N-acetylgalactosaminyltransferases and the primary structure of the genes encoding these enzymes. The present invention meets this need, and further presents other related advantages.

SUMMARY OF THE INVENTION

The present invention provides isolated nucleic acids encoding human UDP-N-acetyl-α-D-galactosamine:polypeptide N-acetylgalactosaminyltransferase (GalNAc-T3), including cDNA and genomic DNA. GalNAc-T3 has a hitherto unknown acceptor substrate specificity, as exemplified by its ability to glycosylate the fibronectin sequence VTHPGY and the HIV-V3 sequence GRAFVTIGKIG. The complete nucleotide sequence of GalNAc-T3, SEQ ID NO: 1, is set forth in FIGS. 3A–3C.

In one aspect, the invention encompasses isolated nucleic acids comprising the nucleotide sequence of nucleotides 991–2889 as set forth in SEQ ID NO: 1 or sequence-conservative or function-conservative variants thereof. Also provided are isolated nucleic acids hybridizable with nucleic acids having the sequence of SEQ ID NO: 1 or fragments thereof or sequence-conservative or function-conservative variants thereof; preferably, the nucleic acids are hybridizable with GalNAc-T3 sequences under conditions of intermediate stringency, and, most preferably, under conditions of high stringency. In one embodiment, the DNA sequence encodes the amino acid sequence, SEQ ID NO:2, also shown in FIGS. 3A–3C, from methionine (amino acid no. 1) to aspartic acid (amino acid no. 633). In another embodiment, the DNA sequence encodes an amino acid sequence comprising a sequence from serine (no. 50) to aspartic acid (no. 633) of SEQ ID NO:2.

In a related aspect, the invention provides nucleic acid vectors comprising GalNAc-T3 DNA sequences, including but not limited to those vectors in which the GalNAc-T3 DNA sequence is operably linked to a transcriptional regulatory element, with or without a polyadenylation sequence. Cells comprising these vectors are also provided, including without limitation transiently and stably expressing cells. Viruses, including bacteriophages, comprising GalNAc-T3-derived DNA sequences are also provided. The invention also encompasses methods for producing GalNAc-T3 polypeptides. Cell-based methods include without limitation those comprising: introducing into a host cell an isolated DNA molecule encoding GalNAc-T3, or a DNA construct comprising a DNA sequence encoding GalNAc-T3; growing the host cell under conditions suitable for GalNAc-T3 expression; and isolating GalNAc-T3 produced by the host cell. A method for generating a host cell with de novo stable expression of GalNAc-T3 comprises: introducing into a host cell an isolated DNA molecule encoding GalNAc-T3 or an enzymatically active fragment thereof (such as, for example, a polypeptide comprising amino acids 50–633 of SEQ ID NO:2), or a DNA construct comprising a DNA sequence encoding GalNAc-T3 or an enzymatically active fragment thereof; selecting and growing host cells in an appropriate medium; and identifying stably transfected cells expressing GalNAc-T3. The stably transfected cells may be used for the production of GalNAc-T3 enzyme for use as a catalyst and for recombinant production of peptides or proteins with appropriate O-glycosylation. For example, eukaryotic cells, whether normal or cancer cells, having their O-glycosylation pattern modified by stable transfection as above, or components of such cells, may be used to deliver specific glyco-forms of glycopeptides and glycoproteins, such as, for example, as immunogens for vaccination.

In yet another aspect, the invention provides isolated GalNAc-T3 polypeptides, including without limitation polypeptides having the sequence set forth in SEQ ID NO:2, polypeptides having the sequence of amino acids 50–633 as set forth in SEQ ID NO:2, and a fusion polypeptide consisting of at least amino acids 50–633 as set forth in SEQ ID NO:2 fused in frame to a second sequence, which may be any sequence that is compatible with retention of GalNAc-T3 enzymatic activity in the fusion polypeptide. Suitable second sequences include without limitation those comprising an affinity ligand or a reactive group.

In another aspect of the present invention, methods are disclosed for screening for mutations in the coding region (exons I-X) of the GalNAc-T3 gene using genomic DNA isolated from, e.g., blood cells of patients. In one embodiment, the method comprises: isolation of DNA from a patient; PCR amplification of coding exons I-X; DNA sequencing of amplified exon DNA fragments and establishing therefrom potential structural defects of the GalNAc-T3 gene associated with disease.

These and other aspects of the present invention will become evident upon reference to the following detailed description and drawings.

BRIEF DESCRIPTION OF THE DRAWINGS

FIG. 1 is a schematic diagram depicting an alignment of GalNAc-transferase amino acid sequences derived from: human GalNAc-T1 (accession # X85018), human GalNAc-T2 (accession # X85019), a C. elegans gene (accession # L16621), and GalNAc-T3 according to the present invention. A 61 amino acid motif with high sequence similarity is shown, wherein an asterisk (*) indicates an identical amino acid or base. Also shown are the location and sequence of primers (designated EBHC100/EBHC106) that were used to clone GalNAc-T3 DNA.

FIG. 2 is an illustration of an agarose gel in which GalNAc-T3-specific reverse transcriptase-polymerase chain reaction (RT-PCR) products have been resolved. The primers used for the RT-PCR reaction were EBHC100/EBHC106. The source of RNA used for the RT-PCR reaction is indicated for each lane. The migration of PhiX174 DNA markers (194 and 118 bp) is indicated in the leftmost lane, and the predicted RT-PCR product of EBHC100/EBHC106 (196 bp) as well as the larger product of a BstNI cleavage hereof (128 bp) are indicated at right.

FIGS. 3A–3C depict the DNA sequence of the GalNAc-T3 gene and the predicted amino acid sequence of GalNAc-T3. The amino acid sequence is shown in single letter code. The hydrophobic segment representing the putative transmembrane domain is double underlined, and adjacent charged amino acids are single-stipple underlined. Potential N-linked glycosylation sites are indicated by an asterisk. The locations of primers used for RT-PCR preparation of the expression construct are indicated by single underlining. The GalNAc-transferase motif is indicated in bold typeface at the amino acid level, and primers EBHC100/EBHC106 are indicated in bold typeface at the nucleotide level.

FIGS. 4A–4B are an illustration of a sequence comparison between human GalNAc-T1 (T1), human GalNAc-T2 (T2), human GalNAc-T3 (T3), and a homologous C. elegans gene (EMBL accession # L16621). Cysteine residues are indicated by boldface type and underlining, and cysteine residues aligned between sequences are indicated by a box.

FIG. 7 is a photographic illustration of fluorescence localization of GalNAc-T3 gene to chromosome 2q24–31 using in situ hybridization.

FIGS. 8A–8C are a schematic representation of forward and reverse PCR primers that can be used to amplify different regions of the GalNAc-T3 gene. The sequences of the primers are also shown.

DETAILED DESCRIPTION OF THE INVENTION

Figure 5:
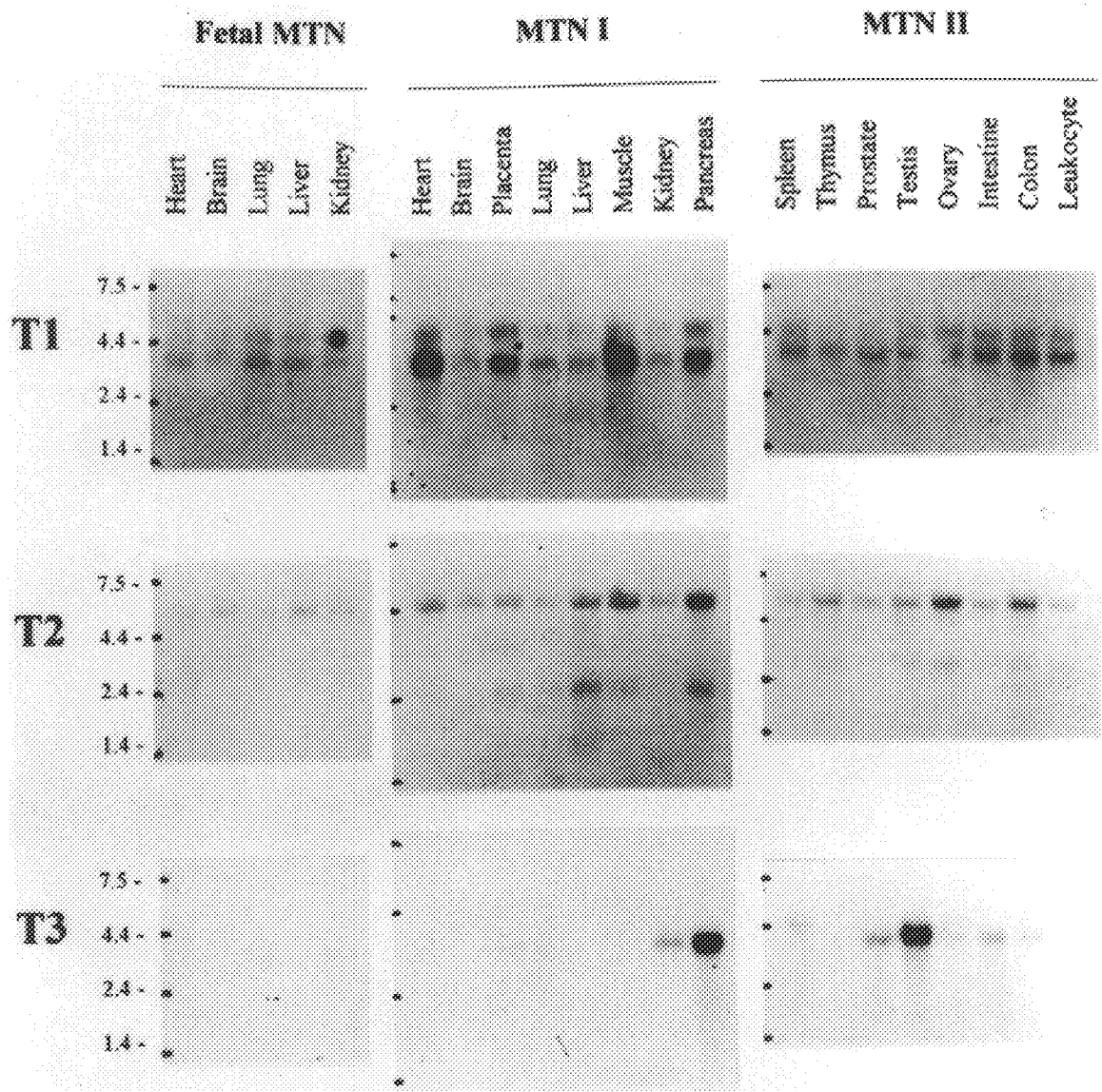
FIG. 5 is a photographic illustration of Northern blot analysis of the expression patterns of GalNAc-T1, GalNAc-T2, and GalNAc-T3 in different tissues. MTN signifies Multiple Tissue Northern blots (Clonetech).

All patent applications, patents, and literature references cited in this specification are hereby incorporated by reference in their entirety. In the case of conflict, the present description, including definitions, is intended to control.

Definitions:

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA—DNA, DNA—RNA and RNA—RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in an mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15M NaCl, 0.015M Na citrate.)

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of GalNAc-T3 are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., an N-acetylgalactosaminyltransferase and that contributes an N-acetylgalactosyl moiety for the transferase reaction. For GalNAc-T3, a donor substrate is UDP-N-acetylgalactosamine. An "acceptor substrate" is a molecule, preferably a peptide or polypeptide, that is recognized by, e.g., an N-acetylgalatosaminyltransferase and that is the target for the modification catalyzed by the transferase, i.e., receives the N-acetylgalatosyl moiety. For GalNAc-T3, acceptor substrates include without limitation peptides comprising the sequence VTHPGY and GRAFVTIGKIG.

The present invention provides the isolated DNA molecules, including genomic DNA and cDNA, encoding the UDP-N-acetyl-α-D-galactosamine:polypeptide N-acetylgalactosaminyltransferase, GalNAc-T3. Based on sequence similarities identified between GalNAc-T1, -T2, and a *C. elegans* homologue, a RT-PCR strategy was used for the cDNA cloning of GalNAc-T3. The cloning strategy may be briefly summarized as follows: 1) synthesis of degenerate oligonucleotides flanking GalNAc-transferase motif, designated EBHC100 and EBHC106; 2) cDNA preparation; 3) polymerase chain reaction (PCR) amplification; 4) identification of a novel cDNA sequence corresponding to GalNAc-T3; 5) construction and screening of cDNA sublibraries by PCR; 6) expression of the cDNA encoding GalNAc-T3 in Sf9 (*Spodoptera frugiperda*) cells. More specifically, the isolation of a representative DNA molecule encoding a novel third member of the UDP-N-acetyl-α-D-galactosamine:polypeptide N-acetylgalactosaminyltransferase family involved the following procedures described below.

Identification of DNA homologous to GalNAc-T1 and -T2.

A set of primers, designated EBHC100/EBHC106 (see FIG. 1), corresponding to sequences that flank a putative GalNAc-transferase sequence motif (FIG. 1) was used in RT-PCR reactions with mRNA from a variety of human organs and cell lines. A single DNA fragment of approximately 196 bp, which corresponds to that predicted for GalNAc-T1 and -T2, was amplified from all templates (FIG. 2). Hybridization with oligonucleotide probes specific for GalNAc-T1 and -T2 served as controls for the identities of the products observed. A restriction enzyme (BstNI) that selectively cut the products of both GalNAc-T1 and -T2 was used to distinguish hitherto unidentified DNA from homologous genes.

As seen in FIG. 2, RNA from several organs and cell lines yielded RT-PCR products that were not cleaved by BstNI, indicating the presence of a novel DNA fragment. The BstNI-uncleaved RT-PCR product from the gastric carcinoma cell line MKN45 was subcloned and sequenced. Forty independent clones were sequenced, and of these, eight clones contained sequences related to, but distinct from, GalNAc-T1 and -T2. Six independant clones had a novel sequence designated TE3 and two clones had a novel sequence designated TE4.

The DNA sequence of TE3 was clearly similar to GalNAc-T1 and -T2, with a sequence similarity of approximately 80%. The deduced amino acid sequence containing the putative GalNAc-transferase motif of T3 is presented in FIG. 1.

Cloning of human GalNAc-T3 using the TE3 DNA sequence.

Cloning and sequencing of full length GalNAc-T3 was achieved by PCR amplification of a cDNA library (Clontech) using primers derived from the TE3 sequence shown in FIGS. 3A–3C, in combination with primers flanking the λgt11 cDNA cloning site. Forty sublibraries were screened by PCR. Thirteen sublibraries were positive for TE3 sequences. Subdividing the cDNA library facilitated identification of clones with long 5' and 3' inserts. Furthermore, this strategy allowed the comparison of multiple 5' and 3' sequences obtained within the isolated cDNA clones to identify and avoid intron-containing sequences.

Two 3' PCR products of 1000 bp and two 5' PCR products of 1200 bp were selected, subcloned and sequenced. The sequences exhibited similarity to GalNAc-T1 and -T2. The respective λcDNA clones were isolated and inserts subcloned and sequenced for confirmation. The 3' cDNA clone designated #8;3' possessed a 3 kbp insert with a single 900 bp open reading frame followed by multiple stop codons and a consensus polyadenylation box. The 5' end of the insert of clone #8;3' apparently contained an intron sequence and this was later confirmed by sequence comparison of several RT-PCR and cDNA clones as well as a genomic clone. One 5' cDNA clone (designated #1;5') possessed a 1300 bp open reading frame, but was not considered to be full length because it lacked a putative hydrophobic transmembrane region. A second screen using an anti-sense primer EBHC211 (5' region of clone #1;5') yielded another 5' clone (#12;5'), which contained additional 550 bp of 5' sequence including a potential transmembrane region.

FIGS. 3A–3C shows the composite sequences of the selected cDNA clones, which yielded a 1902 bp open reading frame. Multiple alignment analysis (DNASIS, Hitachi) of human GalNAc-T1, -T2, -T3, and the *C. elegans* gene presented in FIGS. 4a–4B demonstrated sequence similarity in the 80% C-terminal region and conservation of cysteine residues. The N-terminal regions show no sequence similarity and vary considerably in length, with GalNAc-T3 having the longest sequence between the putative transmembrane region and putative catalytic domain.

Expression of GalNAc-T3.

Expression of the pAcGP67-GalNAc-T3-sol construct in Sf9 cells (Pharmingen Via AH Diagnostics, Denmark) resulted in significant increases in GalNAc-transferase activity in the culture medium of infected cells compared to uninfected controls or cells infected with the histo-blood group O2 gene (Table I).

TABLE I

Expression of GalNAc-T3 in Sf9-cells

| Constructs | Specific activity, m units/mL* | | |
|---|---|---|---|
| | Muc2 | Muc5 | HIV-V3 |
| pAcGP67-GalNAc-T3-sol | 2.05 | 0.77 | 0.97 |
| pAcGP67-GalNAc-T1-sol | 1.98 | 1.24 | 0.03 |
| pAcGP67-GalNAc-T2-sol | 1.20 | 0.66 | 0.02 |
| pAcGP67-O$^2$-sol | 0.08 | 0.02 | 0.01 |
| uninfected cells | 0.12 | 0.04 | 0.01 |

*One unit of enzyme is defined as the amount of enzyme that transfer 1 μmol GalNAc in one min using a standard reaction mixture with 50 μg peptide as acceptor substrate. The sequence and source for Muc2, Muc5, and V3 are described in Example 2 below.

GalNAc-transferase activity with the Muc2 acceptor substrate peptide was increased 20-fold, and activity with the HIV-V3 peptide was increased nearly 100-fold. In contrast, expression of GalNAc-T1 and -T2 constructs only increased the GalNAc-transferase activity toward Muc2 and Muc5C peptide substrates. This illustrates the unique acceptor substrate specificity of GalNAc-T3.

Background levels of GalNAc-transferase actvity in untransfected cell medium were higher than in control transfected cell medium, probably as a result of the production and release of endogenous Sf9 GalNAc-transferase due to the larger number of cells in untransfected cultures. Furthermore, background enzyme activity varied significantly among different acceptor substrate peptides. The peptide Muc2 yielded the highest background and HIV-V3 peptide yielded the lowest activity.

Northern blot analysis of human organs.

Multiple tissue northern blots (MTN) containing mRNA from sixteen human adult and 5 fetal organs (Clontech) were probed with GalNAc-T1, -T2, and -T3 (FIG. 5). Similar to previous results (Homa et al. 1993), GalNAc-T1 hybridized to two mRNAs of approximately 3.4 and 4.1 kb present in MTN I blots, whereas GalNAc-T2 hybridized to a 4.5 kb mRNA. Variable amounts of a smaller 2–3 kb mRNA were also detected with this probe (White et al. 1995). Hybridization of these probes to MTN II and fetal MTN blots resulted in slightly different estimated mRNA sizes for all GalNAc-T's (FIG. 5). This discrepancy is probably due to differences in the parameters of gel electrophoresis and the marker positions assigned by the supplier. GalNAc-T3 hybridized to a 3.6 kb mRNA (estimated from MTN I), which is highly expressed in pancreas and testis and weakly expressed in kidney, prostate, ovary, intestine and colon. A very low level of GalNAc-T3 mRNA was also detected in adult placenta and lung as well as fetal lung and kidney. In adult spleen GalNAc-T3 hybridized to a larger 4.2 kb mRNA (estimated from MTN II). These results demonstrate tissue-specific expression of GalNAc-T3, which contrasts with the expression patterns of T1 and T2.

Genomic organization of GalNAc-T3 gene.

Figure 6:
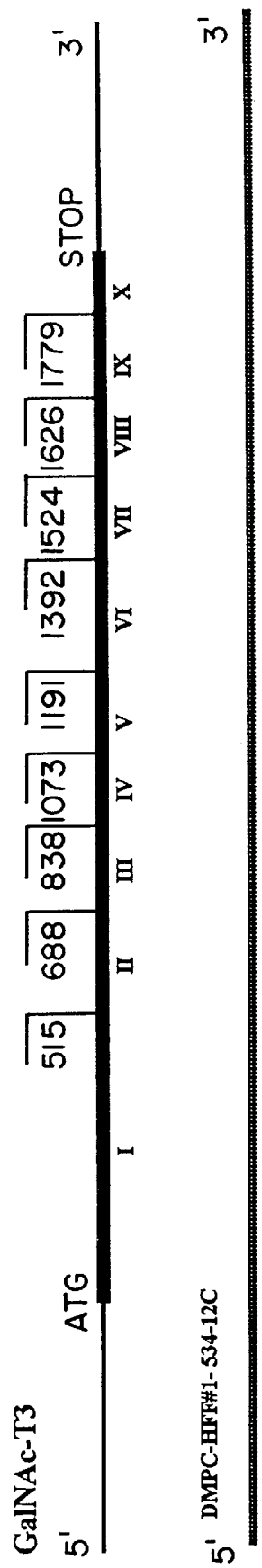
FIG. 6 is a schematic representation of the genomic structure of the coding region of the human GalNAc-T3 gene. The nine identified introns (I-IX) are indicated, as are the nucleotide positions of the 3' exon boundaries.

The present invention also provides isolated genomic DNA molecules encoding GalNAc-T3. A human P1 library (Genome Systems, St. Louis, Mo.) was screened using a PCR probe based on two primers, EBHC205/EBHC211, located in coding exon 1 yielding a product of 120 bp. A single clone DMPC-HFF#1-534-12C was isolated and Southern blot analysis with various oligonucleotides covering the 3' and 5' coding sequence of the existing full length GalNAc-T3 cDNA indicated that the entire coding sequence was included in the P1 clone. A comparative Southern blot analysis between cloned P1 DNA and total human genomic DNA using a full length cDNA as probe giveS identical/similar patterns, validating the use of cloned P1 DNA as a model. The P1 clone was partially sequenced and nine introns identified as shown in FIG. 6. All exon/intron boundaries identified conform to the GT-AG consensus rule (Brethnach 1979).

Chromosomal localization of GalNAc-T3 gene.

The present invention also discloses the chromosomal localization of the GalNAc-T3 gene. Fluorescence in situ hybridization to metaphase chromosomes using the isolated P1 phage showed fluorescence signals at 2q24–31 (FIG. 7; 20 metaphases evaluated). No specific hybridization was observed at any other chromosomal site.

The GalNAc-T3 gene according to the present invention is a candidate gene for a recently identified insulin-dependent diabetes melitus susceptibility gene (IDDM7) localized to chromosome 2q31–33 (Copeman et al., 1995; Luo et al., 1995). The GalNAc-T3 gene is selectively expressed in pancreas, the target organ of diabetes type 1 autoimmunity, and co-localizes to chromosome 2q31. The GalNAc-T3 enzyme of the present invention was shown to exhibit O-glycosylation capacity beyond that of GalNAc-T1 and -T2, implying that the GalNAc-T3 gene is vital for correct/full O-glycosylation in vivo as well. A structural defect in the GalNAc-T3 gene leading to a deficient enzyme or completely defective enzyme would therefore expose a cell or an organism to protein/peptide sequences which were not covered by O-glycosylation as seen in cells or organisms with intact GalNAc-T3 gene. These findings strongly suggest that the GalNAc-T3 gene represents IDDM7. Described in Example 6 below is a method for scanning the ten coding exons for potential structural defects. Similar methods could be used for the characterization of defects in the non-coding region of the GalNAc-T3 gene including the promoter region.

DNA, Vectors, and Host Cells

In practicing the present invention, many conventional techniques in molecular biology, microbiology, recombinant DNA, and immunology, are used. Such techniques are well known and are explained fully in, for example, Sambrook et al., 1989, *Molecular Cloning: A Laboratory Manual*, Second Edition, Cold Spring Harbor Laboratory Press, Cold Spring Harbor, New York; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes* 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I-IV (Weir and Blackwell eds.).

The invention encompasses isolated nucleic acid fragments comprising all or part of the nucleic acid sequence disclosed herein as SEQ ID NO:1. The fragments are at least about 8 nucleotides in length, preferably at least about 12 nucleotides in length, and most preferably at least about 15–20 nucleotides in length. The invention further encompasses isolated nucleic acids comprising sequences that are hybridizable under stringency conditions of 2×SSC, 55° C., to SEQ ID NO: 1; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'- noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences designated SEQ ID NO: 1 or sequence-conservative or function-conservative variants thereof, or a complement thereof, and that has been labelled as described above.

The invention also provides nucleic acid vectors comprising the disclosed sequence or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, liposome-mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *Saccharomyces cerevisiae, Schizosaccharomyces pombi*, SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced GalNAc-T3 derived peptides and polypeptides.

Advantageously, vectors may also include a transcription regulatory element (i.e., a promoter) operably linked to the GalNAc-T3-coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild-type or variant GalNAc-T3 polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use, for example, as probes for the detection of GalNAc-T3 in other species and as templates for the recombinant production of peptides or polypeptides. These and other embodiments of the present invention are described in more detail below.

Polypeptides and Antibodies

The present invention encompasses isolated peptides and polypeptides encoded by the disclosed GalNAc-T3 DNA sequence. Peptides are preferably at least five residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of Matteucci et al., 1981, *J. Am. Chem. Soc.* 103:3185, the method of Yoo et al., 1989, *J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well-known in the art, including, without limitation, preparative disc-gel elctrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of GalNAc-T3 polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that specifically recognize immunogenic components derived from GalNAc-T3. Such antibodies can be used as reagents for detection and purification of GalNAc-T3.

GalNAc-T3 specific antibodies according to the present invention include polyclonal and monoclonal antibodies. The antibodies may be elicited in an animal host by immunization with GalNAc-T3 components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well-known in the art. For example, techniques for producing and processing polyclonal antisera are disclosed in Mayer and Walker, 1987, *Immunochemical Methods in Cell and Molecular Biology*, (Academic Press, London).

The antibodies of this invention can be purified by standard methods, including but not limited to preparative disc-gel elctrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification*, 1989, Amicon Division, W. R. Grace & Co. General protein purification methods are described in *Protein Purification: Principles and Practice*, R. K. Scopes, Ed., 1987, Springer-Verlag, New York, N.Y.

Anti-GalNAc-T3 antibodies, whether unlabeled or labeled by standard methods, can be used as the basis for immunoassays. The particular label used will depend upon the type of immunoassay used. Examples of labels that can be used include, but are not limited to, radiolabels such as $^{32}$P, $^{125}$I, $^{3}$H and $^{14}$C; fluorescent labels such as fluorescein and its derivatives, rhodamine and its derivatives, dansyl and umbelliferone; chemiluminescers such as luciferia and 2,3-dihydrophthal-azinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described in, e.g., Chan (Ed.), 1987, *Immunoassay: A Practical Guide*, Academic Press, Inc., Orlando, Fla.

The following examples are intended to further illustrate the invention without limiting its scope.

EXAMPLE 1

A: Identification of cDNA homologous to GalNAc-T1 and -T2 by RT-PCR and restriction enzyme analysis.

Multiple sequence alignment analysis (DNASIS, Hitachi) of GalNAc-T1 and -T2 was applied to identify areas with highest degree of sequence similarity. Based upon a 61 amino acid segment shared by GalNAc-T1 and -T2 as well as a more recently reported homologous gene from *C. elegans* (EMBL accession # L16621), a pair of sense and anti-sense primers (EBHC100 5'-TGGGGAGGAGARAACCTAGA-3' SEQ ID NO:5 and EBHC106 5'-ATTCATCCATCCATACTTCT-3' SEQ ID NO:6, respectively, was used in RT-PCR amplifications of poly (A+)RNA from several sources (FIGS. 1 and 2). The mRNA from human organs (liver, brain, and submaxillary gland) were obtained from Clontech and mRNA from human cancer cell lines (MKN45, Colo205, and WI38) prepared using a standard guanidine-thiocyanate procedure. A restriction enzyme search identified a common BstNI site within the expected 196 bp RT-PCR product of GalNAc-T1 and -T2 which would produce two fragments of 128 and 68 bp. Novel DNA fragments representing putative additional GalNAc-transferases were identified by RT-PCR with EBHC100/EBHC106 primers. Six mRNA templates were analysed after BstNI digestion in 2% agarose gels. Following reverse transcription using the EBHC106 primer, PCR was performed for 35 cycles of 95° C., 45 s; 53° C., 15 s; 72° C., 15 s; using Taq polymerase on a model 480 thermocycler (Perkin Elmer). Products were verified by Southern blotting and hybridization with oligonucleotide probes specific for GalNAc-T1 or -T2 (EBHC 112: 5'-CTTTGGAAATTGTTACATGCTCA-3' SEQ ID NO:7 and EBHC45:5'-TGGTGGCAGCCTGGAGATCA-3' SEQ ID NO:8, respectively). The 196 bp products from RT-PCR of MKN45 mRNA that were resistant to BstNI cleavage were isolated using the prep-A-gene kit (BIO-RAD) and cloned into the pT7T3U19 vector (Pharmacia). Plasmids from 40 individual clones were purified using tip 20 (QIAGEN) and the clones sequenced. Two sets of sequences differing from GalNAc-T1 and -T2 but exhibiting a high degree of similarity were identified, and sequence information from one set of identical clones designated TE3 was used for the isolation of 5' and 3' sequences outside the GalNAc-transferase motif.

B: Cloning and sequencing of GalNAc-T3 by rapid cDNA library screening.

A PCR screening strategy using oligonucleotide primer pairs derived from the TE3 sequence and the λgt11 vector sequence flanking the insert yielded cDNA clones containing additional 5' and 3' sequences. Primers EBHC202 (5'-GCGGATCCGCAGCAAAAGCCCTCATAGCTTT-3' SEQ ID NO:9) and EBHC204 (5'-GCGGATCCTCTAGCAATCACCTGAGTGCC-3' SEQ ID NO:10) with BamHI sites introduced were combined with either λgt11 forward vector primer (5'-GGTGGCGACGACTCCTGGAGCCCG-3' SEQ ID NO:11) or λgt11 reverse vector primer (5'-TTGACACCAGACCAACTGGTAATG-3' SEQ ID NO:12) for PCR amplification of a human submaxillary gland library (Clontech). Amplifications were performed for 35 cycles of 95° C., 45 s, 55° C., 1 s, 72° C., 2 min. RT-PCR with selected oligonucleotides indicated that TE3 was highly expressed in submaxillary glands, hence the human salivary gland library was used in the screening procedure. The rapid library screening was performed by diluting 1×10⁶ pfu into 40 sublibraries (designated #1-40) each possessing approximately 2.5×10⁴ pfu. All sublibraries were subjected to phage amplification (approx. 40-fold) by liquid culture phage amplification (Sambrook et al. 1989) giving a sublibrary titer of 1×10⁶ pfu. Phage amplification was performed in 1 mL LB MgSO₄ maltose media in a shaking incubator at 37° C. for 5 h. After amplification, 20 mL chloroform was added to each sublibrary, cellular debris was pelleted, and the phage supernatants were titrated and used in subsequent screenings. All 40 sublibraries were screened to identify TE3 possessing phage clones. One mL of each sublibrary approximately $10^4$–$10^5$ pfu was lysed in a 10 mL volume in the presence of 0.45% NP-40 and TWEEN-20, 100 mg/mL proteinase K at 56° C. for 30 min. Proteinase K was heat inactivated by boiling for 15 min and 2 mL of phage lysate was amplified by PCR using primers EBHC100 and EBHC204 at 0.5 mM using 40 cycles of 95° C. for 45 s, 55° C. for 5 s, and 72° C. for 30 s. Thirteen sublibraries possessing TE3 λgt11 clones were selected for further analysis. Each positive sublibrary was screened by PCR using EBHC202 or EBHC204 primers combined with the λgt11 vector primers to determine the length of cDNA inserts.

Two sublibraries generated 3' SEQ ID NO:3 PCR products (EBHC204/λgt11 vector) of approximately 1000 bp, and two sublibraries generated TE3 5' PCR products of approximately 1200 bp. All products were subcloned into pT7T3U19 and sequenced. Clone #8;3' included the entire sequence 3' of a novel gene containing a partial sequence of TE3. The 5' sequence from one clone #1;5' obtained in the first screening and considered to contain only a partial sequence of the 5' end was used to design an additional anti-sense 5' primer EBHC211 (5'-AGCGGATCCAGTGTTTAGCTTCCCCACG-3') which was used with the λgt11 vector primers for PCR amplifications to obtain another clone #12;5' that contained 550 bp of additional 5' sequence. These PCR products were used to probe and isolate cDNA clones from the sublibraries for sequence confirmation. Both strands of the subcloned cDNAs were sequenced (Sanger et al. 1977) using internal primers spaced 3–400 bp apart. Overlapping sequence data were utilized to derive the full length sequence.

C: λ cDNA isolation.

25000 pfu from sublibraries were plated on 15 cm LB agar plates by standard procedures (Sambrook et al. 1989), plaques were transferred to HYBOND N+(Amersham) nylon membranes and hybridized to random primed $\alpha^{32}$P-dCTP labeled PCR probes. Hybridization was performed at 42° C. in the presence of 6×SSPE, 5×Denhart's, 0.5% SDS and 50% formamide. Plaque lifts were washed 5× at 42° C. with 2×SSCX, 0. 1% SDS, once with 0.5×SSCX, 0.1% SDS, and once at 55° C. with 0.1×SSCX, 0.1% SDS, in a mini-hybridization oven (HYBAID).

EXAMPLE 2

A: Expression of GalNAc-T3 in Sf9 cells.

A partial cDNA sequence (pAcGP67-GalNAc-T3-sol) of the putative GalNAc-T3 gene was produced by RT-PCR using primers EBHC219 (5'-AGCGGATCCTCAACGATGGAAAGGAACATG-3' SEQ ID NO:14) and EBHC215 (5'-AGCGGATCCAGGAACACTTAATCATTTTGGC-3' SEQ ID NO:15 ) with BamHI restriction sites introduced. The PCR product was designed to yield a putative soluble form of the GalNAc-T3 protein with an N-terminal end positioned immediately C-terminal to the potential transmembrane domain and including the entire sequence expected to contain the catalytic domain (FIGS. 3A–3C). The PCR product was cloned into a BamHI site of the expression vector pAcGP67 (Pharmingen), and the expression construct was sequenced to verify the sequence and correct insertion into the cloning site. Control constructs included pAcGP67-GalNAc-T2-sol prepared as described (White et al. 1995), pAcGP67-GalNAc-T1-sol prepared similarly by RT-PCR with human submaxillary gland mRNA and designed to mimic the originally identified amino-terminus of the soluble bovine GalNAc-transferase protein (Homa et al. 1993), and pAcGP67-O²-sol containing the histo-blood group O² cDNA and prepared as described for the blood group A cDNA (Bennett et al. 1995). Co-transfection of Sf9 cells with pAcGP67-constructs and Baculo-Gold™ DNA was performed according to the manufacturer's description.
B: Analysis of polypeptide GalNAc-transferase T3 activity.

GalNAc-transferase activity in culture supernatants were assayed 5 days after transfection of Sf9 cells. Controls included untransfected Sf9 cell culture medium and a construct pAcGP67-O2-sol of the enzymically non-functional histo-blood group O² gene (Grunnet et al. 1994). GalNAc-transferase activity was measured in standard reaction mixtures containing 25 mM Tris (pH 7.4), 5 mM MnCl$_2$, 0.25% "Triton X-100", 50 µM UDP-[$^{14}$C]-GalNAc(4000 cpm/nmol), 5 mM 2-mercaptoethanol, 250 µM peptide, and 10 µL culture supernatant after incubation at 37° C. for 20 minutes. Acceptor peptides (Muc2: PTTPISTTTMVTPTPTPTC SEQ ID NO:16, Muc5c: CTTSTTSAPTTSTTSAPTTS SEQ ID NO:17, HIV-V3: CIRIQRGPGRAFVTIGKIGNM SEQ ID NO:18) were obtained from Carlbiotech (Copenhagen) and Neosystems (Strasbourg), and quality was ascertained by amino acid analysis and mass spectrometry. Glycosylated product was quantified by scintillation counting after "Dowex- 1" chromatography. All combinations of enzyme sources and peptides were evaluated at least once by C-18 reverse phase chromatography (PC3.2/3 or uRPC C2/C18 SC2.1/10 Smart System, Pharmacia) and scintillation counting of peptide peak fractions to confirm incorporation of $^{14}$C-GalNAc into the acceptor peptide. Preparative glycosylation of the HIV-V3 peptide was performed with 50 nmol peptide, 0.25 mmol UDP-[$^{14}$C]-GalNAc (200 cpm/nmol) in a final volume of 100 mL. Reactions were incubated for 24 hours at 37° C. The glycosylated product was purified by reverse phase C-18 chromatography (Aquabore 10×1 mm, Microbore HPLC, Applied Biosystems).
C: Stable expression of full coding sequence of GalNAc-T3 in CHO cells.

A cDNA sequence encoding the full coding sequence of the putative GalNAc-T3 gene was derived by RT-PCR using primers EBHC 249 (5'-AGCGGATCCTGAATAGCTACTAATACCATCG-3' SEQ ID NO:19) and EBHC 215 with BamHI restriction sites introduced. The PCR product was designed to yield a GalNAc-T3 protein with a hydrophobic transmembrane retention signal in order to have the enzyme expressed and positioned in the appropriate Golgi compartment of the transfected cell. The PCR product was inserted into the BamHI site of a mammalian expression vector pREP9 (Invitrogen), and the construct, pREP9-GalNAc-T3-mem, was transfected into CHO and stable transfectants were selected.
D: Stable expression of the soluble form of GalNAc-T3 in CHO cells.

cDNA pAcGP67-GalNAc-T3-sol containing the coding sequence of the putative soluble GalNAc-T3 enzyme was cloned into the BamHI site of a modified mammalian expression vector pREP9 (Invitrogen). pREP9 had been modified by insertion of an interferon signal peptide sequence into the KpnI/BamHI site of pREP9 ensuring secretion of the expressed product when cloned into the vector. The pREP9-αINF-GalNAc-T3-sol construct was transfected into CHO cells and stable transfectants were selected.

EXAMPLE 3
Restricted organ expression pattern of GalNAc-T3

Multiple tissue Northern (MTN) blots were obtained from Clonetech. The GalNAc-T1 probe, TEB1, was prepared by RT-PCR and contained coding nucleotides 1–1132 (Genbank® accession no. X85018). The GalNAc-T2 probe, TEB2, was prepared as described (White et al. 1995) and contained coding nucleotides 331–1268 (Genbank® accession no. X85019). The GalNAc-T3 probe, TEB3, contained coding nucleotides 307–1902 as shown in FIGS. 3A–3C (corresponding to nucleotides 1138–2889 in SEQ ID NO:1). Probes were random prime labeled using α32PdCTP (Amersham) and oligo labeling kit (Pharmacia). Blots were probed sequentially with GalNAc-T1, -T2, and -T3 probes using the same conditions as were used for plaque lift hybridizations. Blots were probed, stripped and reprobed as recommended by Clontech.

EXAMPLE 4
Genomic structure of the coding region of GalNAc-T3

All exon/intron boundaries were assessed by comparing the cDNA sequence to sequences generated from sequence reactions of genomic P1 clone with primers designed to establish both 5' and 3' intron/exon boundaries of all introns. Thus, oligonucleotides directed both in the sense and anti-sense orientation were utilized to establish all exon/intron splice junctions. Nine introns with positions as shown in FIG. 6 were identified indicating that the coding region is in at least 10 exons.

EXAMPLE 5
Chromosomal localization of GalNAc-T3

In situ hybridization to metaphase chromosomes: P1 DNA was labeled with biotin-14-dATP using the bio-NICK system (Life Technologies). The labeled DNA was precipitated with ethanol in the presence of herring sperm DNA. Precipitated DNA was dissolved and denatured at 80° C. for 10 min followed by incubation for 30 min at 37° C. and added to heat-denatured chromosome spreads where hybridization was carried out overnight in a moist chamber at 37° C. After posthybridization washing (50% formamide, 2×SSC at 42° C.) and blocking with nonfat dry milk powder, the hybridized probe was detected with avidin-FITC (Vector Laboratories) followed by two amplification steps using rabbit-anti-FITC (Dako) and mouse-anti-rabbit FITC (Jackson Immunoresearch). Chromosome spreads were mounted in antifade solution with blue dye DAPI.

EXAMPLE 6
Analysis of DNA polymorphism of GalNAc-T3 gene

Primer pairs as described in FIGS. 8A–8C have been used for PCR amplification of individual coding sequence of the 10 exons. Each PCR product (sizes given in FIGS. 8A–8C) was subcloned and the sequence of 10 clones containing the appropriate insert was determined assuring that both alleles of each individual are characterized.

From the foregoing it will be evident that, although specific embodiments of the invention have been described herein for purposes of illustration, various modifications may be made without deviating from the spirit and scope of the invention.

REFERENCES

Bennett, E. P., Steffensen, R., Clausen, H., Weghuis, D. O., and van Kessel, D. G. (1995) *Biochem Biophys Res Commun* 206, 318–325.

Clausen, H., Pallesen, T., White, T., Wandall, H., and Hansen, J-E. S. (1994) Simple mucin type O-glycans of HIV: enzymatic prediction of glycosylation sites for vaccine construction. In: *Complex Carbohydrates in Drug Research. Structural and Functional Aspects*, edited by Bock, K., and Clausen, H. Munksgaard, Copenhagen.

Copeman, J. B., Cucca, F., Hearne, C. M., Cornall, R. J., Reed, P. W., Ronningen, K. S., Undlien, D. E., et al. (1995) *Nat Genet* 9, 80–95.

Grunnet, N., Steffensen, R., Bennett, E. P., and Clausen, H. (1994) *Vox Sang* 67, 210–215.

Hagen, F. K., Wuyckhuyse Van, B., and Tabak, L. A. (1993) *J Biol Chem* 268, 18960–18965.

Homa, F. L., Hollanders, T., Lehman, D. J., Thomsen, D. R., and Elhammer, A. P. (1993) *J Biol Chem* 268, 12609–12616.

Kleene, R., and Berger, E. G. (1993) *Biochim Biophys Acta* 1154, 283–325.

Lis, H., and Sharon, N. (1993) *Eur J Biochem* 218, 1–27.

Luo, D-F., Bui, M. M., Muir, A, Maclaren, N. K., Thomson, G., and She, J-X. (1995) *J Hum Genet* 57, 911–919.

Matsuura, H., Greene, T., and Hakomori, S. (1989) *J Biol Chem* 264, 10472–10476.

Matsuura, H., Takio, K., Titani, K., Greene, T., Levery, S. B., Salyan, M. E. K., and Hakomori, S. (1988) *J Biol Chem* 263, 3314–3322.

Parekh, R. B. (1994) *Adv Drug Del Rev* 13, 251–266.

Sambrook, J., E. F. Fritsch and T. Maniatis. *Molecular Cloning. A Laboratory Manual*. USA:Cold Spring Harbor Laboratory Press, 1989.

Sanger, F., Miklen, S., and Coulson, A. R. (1977) *Proc Natl Acad Sci USA* 74, 5463–5467.

Schachter, H. (1994) Molecular cloning of glycosyltransferase genes. In: *Molecular Glycobiology*, edited by Fukuda, M., and Hindsgaul, O. IRL Press Oxford, Oxford, p. 88–162.

Sørensen, T., White, T., Wandall, H. H., Kristensen, A. K., Roepstorff, P., and Clausen, H. (1995) *J Biol Chem* 270, 24166–24173.

Varki, A. (1993) Glycobiology 3, 97–130.

White, T., Bennett, E. P., Takio, K., Sørensen, T., Bonding, N., and Clausen, H. (1995) *J Biol Chem* 270, 24156–24165.

We claim:

1. An isolated nucleic acid encoding human UDP-N-acetyl-α-D-galactosamine:polypeptide N-acetylgalactosaminyltransferase T3 (GalNAc-T3).

2. The isolated nucleic acid as defined in claim 1, wherein said nucleic acid is DNA.

3. The isolated nucleic acid as defined in claim 2, wherein said DNA is cDNA.

4. The isolated nucleic acid as defined in claim 2, wherein said DNA is genomic DNA.

5. An isolated nucleic acid as defined in claim 1, wherein said nucleic acid comprises the nucleotide sequence of nucleotides 991–2889 as set forth in SEQ ID NO: 1 or a sequence-conservative variant thereof.

6. An isolated nucleic acid which hybridizes under conditions of high stringency with the nucleic acid having the sequence of nucleotides 991–2889 of SEQ ID NO:1.

7. A nucleic acid vector comprising a nucleic acid sequence encoding human GalNAc-T3.

8. A vector as defined in claim 7, wherein said sequence comprises the nucleotide sequence of nucleotides 991–2889 as set forth in SEQ ID NO:1 or a sequence-conservative variant thereof.

9. The vector as defined in claim 8, wherein said sequence encoding GalNAc-T3 is operably linked to a transcriptional regulatory element.

10. A host cell comprising a vector as defined in claim 7.

11. A host cell comprising a vector as defined in claim 9.

12. The host cell as defined in claim 11, wherein said cell is stably transfected with said vector.

13. The host cell as defined in claim 10, wherein said cell produces enzymatically active GalNAc-T3.

14. The host cell as defined in claim 10, wherein said cell is selected from the group consisting of bacterial, yeast, insect, avian, and mammalian cells.

15. The host cell as defined in claim 13, wherein said cell is selected from the group consisting of bacterial, yeast, insect, avian, and mammalian cells.

16. The host cell as defined in claim 15, wherein said cell is sf9.

17. The host cell as defined in claim 15, wherein said cell is CHO.

18. A method for producing human GalNAc-T3 polypeptides, which comprises:

(i) introducing into a host cell an isolated DNA molecule en coding a human GalNAc-T3, or a DNA construct comprising a DNA sequence encoding GalNAc-T3 ;

(ii) growing the host cell under conditions suitable for human GalNAc-T3 expression; and (iii) isolating human GalNAc-T3 produced by the host cell.

19. An isolated nucleotide sequence comprising nucleotides 1138–2889 of SEQ ID NO:1.

20. A nucleic acid vector comprising the nucleotide sequence of claim 19.

21. A host cell comprising the nucleic acid vector of claim 19.

22. An isolated nucleotide sequence comprising nucleotides 2149–2328 of SEQ ID NO:1.

23. A nucleic acid vector comprising the nucleotide sequence of claim 22.

24. A host cell comprising the nucleic acid vector of claim 23.

25. An isolated nucleic acid encoding human UDP-N-acetyl-α-D-galactosamine:polypeptide N-acetylgalactosaminyltransferase T3 (GalNAc-T3), said transferase:

(i) having specificity for a substrate consisting of a peptide sequence GRAFVTIGKIG; and (ii) being highly expressed in pancreas or testis and weakly expressed in kidney, prostate, ovary, intestine or colon.

26. An isolated nucleotide sequence comprising nucleotides selected from the group consisting of nucleotides 991–1505; nucleotides 1506–1678; nucleotides 1679–1828; nucleotides 1829–2063; nucleotides 2064–2180; nucleotides 2181–2382; nucleotides 2383–2514; nucleotides 2515–2615; nucleotides 2616–2768; and nucleotides 2769–2889 of SEQ ID NO:1.

27. A nucleic acid vector comprising the nucleotide sequence of claim 26.

28. A host cell comprising the nucleic acid vector of claim 27.

* * * * *

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 3889 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: Submaxillary gland ( x i ) SEQUENCE DESCRIPTION: SEQ ID NO: 1:

```
TGGCTATCGC  GGCTCATAGT  ATGTAATCGT  TTCCTAAGAA  GTCCGTATTT  TTCTTTTCCT      60

TTGCTCCTGT  TGTCCCATAT  TAGGGTTTAA  TAAACTTGCT  GTCCTGTTCT  TAGGGTCGAT     120

TGCAAGCAAT  ATTTTATCAA  ACCAAATTCT  GCTTTTTAA   CTTTATGACT  TGTATAGGCT    180

CCGTACAGAC  ACTTCAAGTA  AAGCTAATGA  ATTCTCTTTT  TACTATTAGA  TCTTGTATTT    240

GCTGTGAGCT  ATTAAAACTA  GCTGTTATAT  AACAACAAAT  TAAATGCTGT  TGATTTTCTT    300

GTTTTTAGGG  GTTCCTTCAG  GAGTCACAAG  TACTATTGGG  TTGGAAAATC  TGGGAGAATA    360

ATAGTTTACT  TACTGATGAA  ACTGCTGTAT  TATCATTCAT  TAAGCTGGAG  CAGATCACAG    420

TTTGAGGGTA  AACTACATAA  AATGAAGGCC  ACTATTTAG   ATGGATGCCT  GATAGTACTT    480

ATCAGTATAC  CCTTACTTCC  TTATGGAGCT  CTCTTTTTG   TAATTTATTT  AATGAGGTCC    540

TTTGATTCCT  TGGTTATCAA  GTGAAGATAT  TCTTTTTAA   CTCAAAATAT  ATTTATAAAA    600

TTAATTTTAT  ACATAGTATA  TAGTGGATAT  TAGAGTTTAA  AAAGAATGTA  TTTTTTAATG    660
```

```
GAGAGGAATA  TCAATATTTT  TGCAACCCCA  ATAAATTGTA  GTAAATTGTA  ACAATTATTT      720

TCTTCCAAAA  GTGTAATTTT  CTTGAGGACA  AGATATCTTT  GTATTCTCAT  TAACCATAAG      780

AGTACATTGG  TAGCTTATGT  TCAGTTGTTG  GTTAAATGAA  TGAATTGAGC  CATGCCTGTA      840

GGACTGAATA  GCTACTAATA  CCATCGATCA  TTTCTGTTTA  TAGGTACTAC  CATAAAGATA      900

CCTTCTTCTC  AGCAAATCTA  TGATAAAAAA  TATAAGTAAC  AGAAGAAGAA  ATAACTGTTA      960

TTTGTCAAGT  GACAAGCTTT  TAATGTCAGA  ATG GCT CAC CTA AAG CGA CTA GTA        1014
                                    Met Ala His Leu Lys Arg Leu Val
                                      1               5
```

| | | | | | | | | | | | | | | | | |
|---|---|---|---|---|---|---|---|---|---|---|---|---|---|---|---|---|
| AAA | TTA | CAC | ATT | AAA | AGA | CAT | TAC | CAT | AAA | AAG | TTC | TGG | AAG | CTT | GGT | 1062 |
| Lys | Leu | His | Ile | Lys | Arg | His | Tyr | His | Lys | Lys | Phe | Trp | Lys | Leu | Gly | |
| | | 10 | | | | 15 | | | | 20 | | | | | | |
| GCA | GTA | ATT | TTT | TTC | TTT | ATA | ATA | GTT | TTG | GTT | TTA | ATG | CAA | AGA | GAA | 1110 |
| Ala | Val | Ile | Phe | Phe | Phe | Ile | Ile | Val | Leu | Val | Leu | Met | Gln | Arg | Glu | |
| 25 | | | | | 30 | | | | | 35 | | | | | 40 | |
| GTA | AGT | GTT | CAA | TAT | TCC | AAA | GAG | GAA | TCA | AGG | ATG | GAA | AGG | AAC | ATG | 1158 |
| Val | Ser | Val | Gln | Tyr | Ser | Lys | Glu | Glu | Ser | Arg | Met | Glu | Arg | Asn | Met | |
| | | | | 45 | | | | | 50 | | | | | 55 | | |
| AAA | AAC | AAA | AAC | AAG | ATG | TTG | GAT | TTA | ATG | CTA | GAA | GCT | GTA | AAC | AAT | 1206 |
| Lys | Asn | Lys | Asn | Lys | Met | Leu | Asp | Leu | Met | Leu | Glu | Ala | Val | Asn | Asn | |
| | | | 60 | | | | | 65 | | | | | 70 | | | |
| ATT | AAG | GAT | GCC | ATG | CCA | AAA | ATG | CAA | ATA | GGA | GCA | CCT | GTC | AGG | CAA | 1254 |
| Ile | Lys | Asp | Ala | Met | Pro | Lys | Met | Gln | Ile | Gly | Ala | Pro | Val | Arg | Gln | |
| | | 75 | | | | | 80 | | | | | 85 | | | | |
| AAC | ATT | GAT | GCT | GGT | GAG | AGA | CCT | TGT | TTG | CAA | GGA | TAT | TAT | ACA | GCA | 1302 |
| Asn | Ile | Asp | Ala | Gly | Glu | Arg | Pro | Cys | Leu | Gln | Gly | Tyr | Tyr | Thr | Ala | |
| | 90 | | | | | 95 | | | | | 100 | | | | | |
| GCA | GAA | TTG | AAG | CCT | GTC | CTT | GAC | CGT | CCA | CCT | CAG | GAT | TCA | AAT | GCA | 1350 |
| Ala | Glu | Leu | Lys | Pro | Val | Leu | Asp | Arg | Pro | Pro | Gln | Asp | Ser | Asn | Ala | |
| 105 | | | | | 110 | | | | | 115 | | | | | 120 | |
| CCT | GGT | GCT | TCT | GGT | AAA | GCA | TTC | AAG | ACA | ACC | AAT | TTA | AGT | GTT | GAA | 1398 |
| Pro | Gly | Ala | Ser | Gly | Lys | Ala | Phe | Lys | Thr | Thr | Asn | Leu | Ser | Val | Glu | |
| | | | | 125 | | | | | 130 | | | | | 135 | | |
| GAG | CAA | AAG | GAA | AAG | GAA | CGT | GGG | GAA | GCT | AAA | CAC | TGC | TTT | AAT | GCT | 1446 |
| Glu | Gln | Lys | Glu | Lys | Glu | Arg | Gly | Glu | Ala | Lys | His | Cys | Phe | Asn | Ala | |
| | | | 140 | | | | | 145 | | | | | 150 | | | |
| TTC | GCA | AGT | GAC | AGG | ATT | TCT | TTG | CAC | CGA | GAT | CTT | GGA | CCA | GAC | ACT | 1494 |
| Phe | Ala | Ser | Asp | Arg | Ile | Ser | Leu | His | Arg | Asp | Leu | Gly | Pro | Asp | Thr | |
| | | 155 | | | | | 160 | | | | | 165 | | | | |
| CGA | CCT | CCT | GAA | TGT | ATT | GAA | CAA | AAA | TTT | AAG | CGC | TGC | CCT | CCC | CTG | 1542 |
| Arg | Pro | Pro | Glu | Cys | Ile | Glu | Gln | Lys | Phe | Lys | Arg | Cys | Pro | Pro | Leu | |
| | 170 | | | | | 175 | | | | | 180 | | | | | |
| CCC | ACC | ACC | AGT | GTC | ATA | ATA | GTT | TTT | CAT | AAT | GAA | GCG | TGG | TCC | ACG | 1590 |
| Pro | Thr | Thr | Ser | Val | Ile | Ile | Val | Phe | His | Asn | Glu | Ala | Trp | Ser | Thr | |
| 185 | | | | | 190 | | | | | 195 | | | | | 200 | |
| TTG | CTT | AGA | ACT | GTC | CAC | AGT | GTG | CTC | TAT | TCT | TCA | CCT | GCA | ATA | CTG | 1638 |
| Leu | Leu | Arg | Thr | Val | His | Ser | Val | Leu | Tyr | Ser | Ser | Pro | Ala | Ile | Leu | |
| | | | | 205 | | | | | 210 | | | | | 215 | | |
| CTG | AAG | GAA | ATC | ATT | TTG | GTG | GAT | GAT | GCT | AGT | GTA | GAT | GAG | TAC | TTA | 1686 |
| Leu | Lys | Glu | Ile | Ile | Leu | Val | Asp | Asp | Ala | Ser | Val | Asp | Glu | Tyr | Leu | |
| | | | 220 | | | | | 225 | | | | | 230 | | | |
| CAT | GAT | AAA | CTA | GAT | GAA | TAT | GTA | AAA | CAA | TTT | TCT | ATA | GTA | AAA | ATA | 1734 |
| His | Asp | Lys | Leu | Asp | Glu | Tyr | Val | Lys | Gln | Phe | Ser | Ile | Val | Lys | Ile | |
| | | 235 | | | | | 240 | | | | | 245 | | | | |
| GTC | AGA | CAA | AGA | GAA | AGA | AAA | GGT | CTG | ATC | ACT | GCT | CGG | TTG | CTA | GGA | 1782 |
| Val | Arg | Gln | Arg | Glu | Arg | Lys | Gly | Leu | Ile | Thr | Ala | Arg | Leu | Leu | Gly | |
| | 250 | | | | | 255 | | | | | 260 | | | | | |
| GCA | ACA | GTC | GCA | ACA | GCT | GAA | ACG | CTC | ACA | TTT | TTA | GAT | GCT | CAC | TGT | 1830 |

| | | | | | | | | | | | | | | | |
|---|---|---|---|---|---|---|---|---|---|---|---|---|---|---|---|
| Ala | Thr | Val | Ala | Thr | Ala | Glu | Thr | Leu | Thr | Phe | Leu | Asp | Ala | His | Cys |
| 265 | | | | 270 | | | | | 275 | | | | | | 280 |

| GAG | TGT | TTC | TAT | GGT | TGG | CTA | GAA | CCT | CTG | TTG | GCC | AGA | ATA | GCT | GAG | 1878 |
|---|---|---|---|---|---|---|---|---|---|---|---|---|---|---|---|---|
| Glu | Cys | Phe | Tyr | Gly | Trp | Leu | Glu | Pro | Leu | Leu | Ala | Arg | Ile | Ala | Glu | |
| | | | | 285 | | | | 290 | | | | | | 295 | | |

| AAC | TAC | ACG | GCT | GTC | GTA | AGT | CCA | GAT | ATT | GCA | TCC | ATA | GAT | CTG | AAC | 1926 |
|---|---|---|---|---|---|---|---|---|---|---|---|---|---|---|---|---|
| Asn | Tyr | Thr | Ala | Val | Val | Ser | Pro | Asp | Ile | Ala | Ser | Ile | Asp | Leu | Asn | |
| | | | 300 | | | | | 305 | | | | | 310 | | | |

| ACG | TTT | GAA | TTC | AAC | AAA | CCT | TCT | CCT | TAT | GGA | AGT | AAC | CAT | AAC | CGT | 1974 |
|---|---|---|---|---|---|---|---|---|---|---|---|---|---|---|---|---|
| Thr | Phe | Glu | Phe | Asn | Lys | Pro | Ser | Pro | Tyr | Gly | Ser | Asn | His | Asn | Arg | |
| | | 315 | | | | | 320 | | | | | 325 | | | | |

| GGA | AAT | TTT | GAC | TGG | AGT | CTT | TCA | TTT | GGC | TGG | GAG | TCG | CTT | CCT | GAT | 2022 |
|---|---|---|---|---|---|---|---|---|---|---|---|---|---|---|---|---|
| Gly | Asn | Phe | Asp | Trp | Ser | Leu | Ser | Phe | Gly | Trp | Glu | Ser | Leu | Pro | Asp | |
| | 330 | | | | | 335 | | | | | 340 | | | | | |

| CAT | GAG | AAG | CAA | AGA | AGG | AAA | GAT | GAA | ACC | TAC | CCA | ATT | AAA | ACA | CCC | 2070 |
|---|---|---|---|---|---|---|---|---|---|---|---|---|---|---|---|---|
| His | Glu | Lys | Gln | Arg | Arg | Lys | Asp | Glu | Thr | Tyr | Pro | Ile | Lys | Thr | Pro | |
| 345 | | | | 350 | | | | | 355 | | | | | 360 | | |

| ACT | TTT | GCA | GGA | GGA | CTT | TTT | TCC | ATA | TCA | AAA | GAA | TAT | TTT | GAG | TAT | 2118 |
|---|---|---|---|---|---|---|---|---|---|---|---|---|---|---|---|---|
| Thr | Phe | Ala | Gly | Gly | Leu | Phe | Ser | Ile | Ser | Lys | Glu | Tyr | Phe | Glu | Tyr | |
| | | | | 365 | | | | 370 | | | | | 375 | | | |

| ATT | GGA | AGC | TAT | GAT | GAA | GAA | ATG | GAA | ATC | TGG | GGA | GGT | GAA | AAT | ATA | 2166 |
|---|---|---|---|---|---|---|---|---|---|---|---|---|---|---|---|---|
| Ile | Gly | Ser | Tyr | Asp | Glu | Glu | Met | Glu | Ile | Trp | Gly | Gly | Glu | Asn | Ile | |
| | | | 380 | | | | | 385 | | | | | 390 | | | |

| GAA | ATG | TCT | TTC | AGA | GTA | TGG | CAA | TGT | GGT | GGG | CAG | TTG | GAG | ATT | ATG | 2214 |
|---|---|---|---|---|---|---|---|---|---|---|---|---|---|---|---|---|
| Glu | Met | Ser | Phe | Arg | Val | Trp | Gln | Cys | Gly | Gly | Gln | Leu | Glu | Ile | Met | |
| | | 395 | | | | | 400 | | | | | 405 | | | | |

| CCT | TGC | TCT | GTT | GTT | GGA | CAT | GTT | TTT | CGC | AGC | AAA | AGC | CCT | CAT | AGC | 2262 |
|---|---|---|---|---|---|---|---|---|---|---|---|---|---|---|---|---|
| Pro | Cys | Ser | Val | Val | Gly | His | Val | Phe | Arg | Ser | Lys | Ser | Pro | His | Ser | |
| | 410 | | | | | 415 | | | | | 420 | | | | | |

| TTT | CCA | AAA | GGC | ACT | CAG | GTG | ATT | GCT | AGA | AAC | CAA | GTT | CGC | CTT | GCA | 2310 |
|---|---|---|---|---|---|---|---|---|---|---|---|---|---|---|---|---|
| Phe | Pro | Lys | Gly | Thr | Gln | Val | Ile | Ala | Arg | Asn | Gln | Val | Arg | Leu | Ala | |
| 425 | | | | | 430 | | | | | 435 | | | | | 440 | |

| GAA | GTC | TGG | ATG | GAT | GAA | TAC | AAG | GAA | ATA | TTT | TAT | AGG | AGA | AAT | ACA | 2358 |
|---|---|---|---|---|---|---|---|---|---|---|---|---|---|---|---|---|
| Glu | Val | Trp | Met | Asp | Glu | Tyr | Lys | Glu | Ile | Phe | Tyr | Arg | Arg | Asn | Thr | |
| | | | | 445 | | | | | 450 | | | | | 455 | | |

| GAT | GCA | GCA | AAA | ATT | GTT | AAA | CAA | AAA | GCA | TTT | GGT | GAT | CTT | TCA | AAA | 2406 |
|---|---|---|---|---|---|---|---|---|---|---|---|---|---|---|---|---|
| Asp | Ala | Ala | Lys | Ile | Val | Lys | Gln | Lys | Ala | Phe | Gly | Asp | Leu | Ser | Lys | |
| | | | 460 | | | | | 465 | | | | | 470 | | | |

| AGA | TTT | GAA | ATA | AAA | CAC | CGT | CTT | CGG | TGT | AAA | AAT | TTT | ACA | TGG | TAT | 2454 |
|---|---|---|---|---|---|---|---|---|---|---|---|---|---|---|---|---|
| Arg | Phe | Glu | Ile | Lys | His | Arg | Leu | Arg | Cys | Lys | Asn | Phe | Thr | Trp | Tyr | |
| | | 475 | | | | | 480 | | | | | 485 | | | | |

| CTG | AAC | AAC | ATT | TAT | CCA | GAG | GTG | TAT | GTG | CCA | GAC | CTT | AAT | CCT | GTT | 2502 |
|---|---|---|---|---|---|---|---|---|---|---|---|---|---|---|---|---|
| Leu | Asn | Asn | Ile | Tyr | Pro | Glu | Val | Tyr | Val | Pro | Asp | Leu | Asn | Pro | Val | |
| | 490 | | | | | 495 | | | | | 500 | | | | | |

| ATA | TCT | GGA | TAC | ATT | AAA | AGC | GTT | GGT | CAG | CCT | CTA | TGT | CTG | GAT | GTT | 2550 |
|---|---|---|---|---|---|---|---|---|---|---|---|---|---|---|---|---|
| Ile | Ser | Gly | Tyr | Ile | Lys | Ser | Val | Gly | Gln | Pro | Leu | Cys | Leu | Asp | Val | |
| 505 | | | | | 510 | | | | | 515 | | | | | 520 | |

| GGA | GAA | AAC | AAT | CAA | GGA | GGC | AAA | CCA | TTA | ATT | ATG | TAT | ACA | TGT | CAT | 2598 |
|---|---|---|---|---|---|---|---|---|---|---|---|---|---|---|---|---|
| Gly | Glu | Asn | Asn | Gln | Gly | Gly | Lys | Pro | Leu | Ile | Met | Tyr | Thr | Cys | His | |
| | | | | 525 | | | | | 530 | | | | | 535 | | |

| GGA | CTT | GGG | GGA | AAC | CAG | TAC | TTT | GAA | TAC | TCT | GCT | CAA | CAT | GAA | ATT | 2646 |
|---|---|---|---|---|---|---|---|---|---|---|---|---|---|---|---|---|
| Gly | Leu | Gly | Gly | Asn | Gln | Tyr | Phe | Glu | Tyr | Ser | Ala | Gln | His | Glu | Ile | |
| | | | 540 | | | | | 545 | | | | | 550 | | | |

| CGG | CAC | AAC | ATC | CAG | AAG | GAA | TTA | TGT | CTT | CAT | GCT | GCT | CAA | GGT | CTC | 2694 |
|---|---|---|---|---|---|---|---|---|---|---|---|---|---|---|---|---|
| Arg | His | Asn | Ile | Gln | Lys | Glu | Leu | Cys | Leu | His | Ala | Ala | Gln | Gly | Leu | |
| | | 555 | | | | | 560 | | | | | 565 | | | | |

| GTT | CAG | CTG | AAG | GCA | TGT | ACC | TAC | AAA | GGT | CAC | AAG | ACA | GTT | GTC | ACT | 2742 |
|---|---|---|---|---|---|---|---|---|---|---|---|---|---|---|---|---|
| Val | Gln | Leu | Lys | Ala | Cys | Thr | Tyr | Lys | Gly | His | Lys | Thr | Val | Val | Thr | |
| | 570 | | | | | 575 | | | | | 580 | | | | | |

| GGA | GAG | CAG | ATA | TGG | GAG | ATC | CAG | AAG | GAT | CAA | CTT | CTA | TAC | AAT | CCA | 2790 |
|---|---|---|---|---|---|---|---|---|---|---|---|---|---|---|---|---|

-continued

```
Gly Glu Gln Ile Trp Glu Ile Gln Lys Asp Gln Leu Leu Tyr Asn Pro
585                 590             595                 600

TTC TTA AAA ATG TGC CTT TCA GCA AAT GGA GAG CAT CCA AGT TTA GTG        2838
Phe Leu Lys Met Cys Leu Ser Ala Asn Gly Glu His Pro Ser Leu Val
                605             610                 615

TCA TGC AAC CCA TCA GAT CCA CTC CAA AAA TGG ATA CTT AGC CAA AAT        2886
Ser Cys Asn Pro Ser Asp Pro Leu Gln Lys Trp Ile Leu Ser Gln Asn
            620             625                 630

GAT  TAAGTGTTCC  TTAAAATTAA  GTTGAAAAG  GAAATATTCT  TTCTCATAAA         2939
Asp

ACTGTGACTA  GGCATACACT  GTAGTTTTG  AAAATTATGC  AAAAGCAGCT  AAATGTAACT  2999

TATTCCAAGT  GCATTTTCT   TATTTATATC TTTATGTAGC  ACTATCTACA  GAAATTCTGC  3059

AAGTTTCTGT  TTCAAAGCAC  AATAACTAGT AATACCAAAG  ACTATTTCAA  AATGTCCAGA  3119

TGTAGGGGAA  GAGATGTTTA  CAGTATGATG AAAATAATTT  TCCAAGTAAA  GTGAAGTTTG  3179

TGTGTTTTGT  ACACTTAGGG  ATATATATAT ATAGCTACAT  TCACACACTC  ACAATTTAAA  3239

ATATTTCCCC  TAGTTTTTTG  GGGGGATAGG AAGAAAGATT  TGTTACTGTA  TTTTTTTAAC  3299

TACATAAAAA  TAGATCAATA  AATGTCAGCA TTGGCCTCTG  TGTACAAACC  AAGAGCTTTT  3359

ACAGATCCAG  AATTTATTAG  TTTAAAATGC AGGTGAACTT  TTTTTTGCGT  TTGGTTTACT  3419

TGTCTGTCAA  ATGTTTCCTT  AAACATGAAA CTGAATAAGG  AGAAGAGTAT  TTTTAACACT  3479

TAAATTTCTT  GGCAAATTTT  AAAACATTTT TTAGTCTGTA  ATACACTCCA  CTTGAAGCAC  3539

TTAAGTCTTC  CTTAAATGAC  TTTTCTTAAG TAATGATACT  GTGTGTTTC   CCAAAGCACT  3599

TTTAAAAAAA  TTTTTATAAA  TTACTATCTG TTGAAAGGT   GTCCTTTCC   TTTCTTCTAG  3659

TATTTTTTTT  CTTACCAAAA  TTCACTAATC TTGAATGTTT  GTGATATTAA  ATTTCAAATG  3719

CAGAATACTT  GACTCATTTA  AAGCTAAATT TTGTTACTGA  TTCAATTATA  ATTGTAATGG  3779

ATTTTTGACT  TTGTAATGGA  TTCTTTTCAT CAAAAAGCCT  TATTTTTTA   TCTATGTGGA  3839

AAACACAATA  AAAAATCCTC  AACACTAAAA AAAAAAAAC   CGGAATTCCG              3889
```

( 2 ) INFORMATION FOR SEQ ID NO: 2:

( i ) SEQUENCE CHARACTERISTICS:
        ( A ) LENGTH: 633 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens
        ( F ) TISSUE TYPE: Submaxillary gland ( x i ) SEQUENCE DESCRIPTION: SEQ ID NO: 2:

```
Met Ala His Leu Lys Arg Leu Val Lys Leu His Ile Lys Arg His Tyr
1               5                   10                  15

His Lys Lys Phe Trp Lys Leu Gly Ala Val Ile Phe Phe Ile Ile
                20              25              30

Val Leu Val Leu Met Gln Arg Glu Val Ser Val Gln Tyr Ser Lys Glu
            35              40              45

Glu Ser Arg Met Glu Arg Asn Met Lys Asn Lys Asn Lys Met Leu Asp
        50              55              60

Leu Met Leu Glu Ala Val Asn Asn Ile Lys Asp Ala Met Pro Lys Met
65              70              75              80

Gln Ile Gly Ala Pro Val Arg Gln Asn Ile Asp Ala Gly Glu Arg Pro
                85              90              95
```

```
Cys  Leu  Gln  Gly  Tyr  Tyr  Thr  Ala  Ala  Glu  Leu  Lys  Pro  Val  Leu  Asp
              100                     105                     110

Arg  Pro  Pro  Gln  Asp  Ser  Asn  Ala  Pro  Gly  Ala  Ser  Gly  Lys  Ala  Phe
              115                     120                     125

Lys  Thr  Thr  Asn  Leu  Ser  Val  Glu  Glu  Gln  Lys  Glu  Lys  Glu  Arg  Gly
         130                     135                     140

Glu  Ala  Lys  His  Cys  Phe  Asn  Ala  Phe  Ala  Ser  Asp  Arg  Ile  Ser  Leu
145                          150                     155                     160

His  Arg  Asp  Leu  Gly  Pro  Asp  Thr  Arg  Pro  Pro  Glu  Cys  Ile  Glu  Gln
                   165                     170                          175

Lys  Phe  Lys  Arg  Cys  Pro  Pro  Leu  Pro  Thr  Thr  Ser  Val  Ile  Ile  Val
                   180                     185                     190

Phe  His  Asn  Glu  Ala  Trp  Ser  Thr  Leu  Leu  Arg  Thr  Val  His  Ser  Val
              195                     200                     205

Leu  Tyr  Ser  Ser  Pro  Ala  Ile  Leu  Leu  Lys  Glu  Ile  Ile  Leu  Val  Asp
         210                     215                     220

Asp  Ala  Ser  Val  Asp  Glu  Tyr  Leu  His  Asp  Lys  Leu  Asp  Glu  Tyr  Val
225                          230                     235                     240

Lys  Gln  Phe  Ser  Ile  Val  Lys  Ile  Val  Arg  Gln  Arg  Glu  Arg  Lys  Gly
                   245                     250                     255

Leu  Ile  Thr  Ala  Arg  Leu  Leu  Gly  Ala  Thr  Val  Ala  Thr  Ala  Glu  Thr
              260                     265                     270

Leu  Thr  Phe  Leu  Asp  Ala  His  Cys  Glu  Cys  Phe  Tyr  Gly  Trp  Leu  Glu
              275                     280                     285

Pro  Leu  Leu  Ala  Arg  Ile  Ala  Glu  Asn  Tyr  Thr  Ala  Val  Val  Ser  Pro
     290                     295                     300

Asp  Ile  Ala  Ser  Ile  Asp  Leu  Asn  Thr  Phe  Glu  Phe  Asn  Lys  Pro  Ser
305                          310                     315                     320

Pro  Tyr  Gly  Ser  Asn  His  Asn  Arg  Gly  Asn  Phe  Asp  Trp  Ser  Leu  Ser
                   325                     330                     335

Phe  Gly  Trp  Glu  Ser  Leu  Pro  Asp  His  Glu  Lys  Gln  Arg  Arg  Lys  Asp
                   340                     345                     350

Glu  Thr  Tyr  Pro  Ile  Lys  Thr  Pro  Thr  Phe  Ala  Gly  Gly  Leu  Phe  Ser
              355                     360                     365

Ile  Ser  Lys  Glu  Tyr  Phe  Glu  Tyr  Ile  Gly  Ser  Tyr  Asp  Glu  Glu  Met
     370                     375                     380

Glu  Ile  Trp  Gly  Gly  Glu  Asn  Ile  Glu  Met  Ser  Phe  Arg  Val  Trp  Gln
385                          390                     395                     400

Cys  Gly  Gly  Gln  Leu  Glu  Ile  Met  Pro  Cys  Ser  Val  Val  Gly  His  Val
                   405                     410                     415

Phe  Arg  Ser  Lys  Ser  Pro  His  Ser  Phe  Pro  Lys  Gly  Thr  Gln  Val  Ile
                   420                     425                     430

Ala  Arg  Asn  Gln  Val  Arg  Leu  Ala  Glu  Val  Trp  Met  Asp  Glu  Tyr  Lys
              435                     440                     445

Glu  Ile  Phe  Tyr  Arg  Arg  Asn  Thr  Asp  Ala  Ala  Lys  Ile  Val  Lys  Gln
     450                     455                     460

Lys  Ala  Phe  Gly  Asp  Leu  Ser  Lys  Arg  Phe  Glu  Ile  Lys  His  Arg  Leu
465                     470                     475                          480

Arg  Cys  Lys  Asn  Phe  Thr  Trp  Tyr  Leu  Asn  Asn  Ile  Tyr  Pro  Glu  Val
                   485                     490                     495

Tyr  Val  Pro  Asp  Leu  Asn  Pro  Val  Ile  Ser  Gly  Tyr  Ile  Lys  Ser  Val
              500                     505                     510

Gly  Gln  Pro  Leu  Cys  Leu  Asp  Val  Gly  Glu  Asn  Asn  Gln  Gly  Gly  Lys
              515                     520                     525
```

| Pro | Leu | Ile | Met | Tyr | Thr | Cys | His | Gly | Leu | Gly | Gly | Asn | Gln | Tyr | Phe |
|---|---|---|---|---|---|---|---|---|---|---|---|---|---|---|---|
| | 530 | | | | | 535 | | | | 540 | | | | | |
| Glu | Tyr | Ser | Ala | Gln | His | Glu | Ile | Arg | His | Asn | Ile | Gln | Lys | Glu | Leu |
| 545 | | | | | 550 | | | | 555 | | | | | | 560 |
| Cys | Leu | His | Ala | Ala | Gln | Gly | Leu | Val | Gln | Leu | Lys | Ala | Cys | Thr | Tyr |
| | | | | 565 | | | | 570 | | | | | 575 | | |
| Lys | Gly | His | Lys | Thr | Val | Val | Thr | Gly | Glu | Gln | Ile | Trp | Glu | Ile | Gln |
| | | | 580 | | | | | 585 | | | | | 590 | | |
| Lys | Asp | Gln | Leu | Leu | Tyr | Asn | Pro | Phe | Leu | Lys | Met | Cys | Leu | Ser | Ala |
| | | 595 | | | | | 600 | | | | | 605 | | | |
| Asn | Gly | Glu | His | Pro | Ser | Leu | Val | Ser | Cys | Asn | Pro | Ser | Asp | Pro | Leu |
| | 610 | | | | | 615 | | | | | 620 | | | | |
| Gln | Lys | Trp | Ile | Leu | Ser | Gln | Asn | Asp | | | | | | | |
| 625 | | | | | 630 | | | | | | | | | | |

(2) INFORMATION FOR SEQ ID NO: 3:

(i) SEQUENCE CHARACTERISTICS:
        (A) LENGTH: 6 amino acids
        (B) TYPE:AMINO
        (B) TYPE:AMINO
        (C) STRANDEDNESS: single
        (D) TOPOLOGY: linear (ii) MOLECULE TYPE: peptide (vi) ORIGINAL SOURCE:
        (A) ORGANISM: Homo sapiens (vii) IMMEDIATE SOURCE:
        (B) CLONE: fibronectin (xi) SEQUENCE DESCRIPTION: SEQ ID NO: 3:

| Val | Thr | His | Pro | Gly | Tyr |
|---|---|---|---|---|---|
| | | | | 5 | |

(2) INFORMATION FOR SEQ ID NO: 4:

(i) SEQUENCE CHARACTERISTICS:
        (A) LENGTH: 11 amino acids
        (B) TYPE:AMINO
        (B) TYPE:AMINO
        (C) STRANDEDNESS: single
        (D) TOPOLOGY: linear (ii) MOLECULE TYPE: peptide (vi) ORIGINAL SOURCE:
        (A) ORGANISM: Homo sapiens (vii) IMMEDIATE SOURCE:
        (B) CLONE: HIV gp120

(xi) SEQUENCE DESCRIPTION: SEQ ID NO: 4:

| Gly | Arg | Ala | Phe | Val | Thr | Ile | Gly | Lys | Ile | Gly |
|---|---|---|---|---|---|---|---|---|---|---|
| | | | | 5 | | | | | 10 | |

(2) INFORMATION FOR SEQ ID NO: 5:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: cDNA to mRNA (vi) ORIGINAL SOURCE:

( A ) ORGANISM: Homo sapiens ( v i i ) IMMEDIATE SOURCE:
( B ) CLONE: EBHC100 primer ( x i ) SEQUENCE DESCRIPTION: SEQ ID NO: 5:

TGGGGAGGAG ARAACCTAGA 20

( 2 ) INFORMATION FOR SEQ ID NO: 6:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC106 primer ( x i ) SEQUENCE DESCRIPTION: SEQ ID NO: 6:

ATTCATCCAT CCATACTTCT 20

( 2 ) INFORMATION FOR SEQ ID NO: 7:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC112 primer ( x i ) SEQUENCE DESCRIPTION: SEQ ID NO: 7:

CTTTGGAAAT TGTTACATGC TCA 23

( 2 ) INFORMATION FOR SEQ ID NO: 8:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC45 primer ( x i ) SEQUENCE DESCRIPTION: SEQ ID NO: 8:

TGGTGGCAGC CTGGAGATCA 20

( 2 ) INFORMATION FOR SEQ ID NO: 9:

( i ) SEQUENCE CHARACTERISTICS:
( A ) LENGTH: 31 bases
( B ) TYPE: nucleic acid
( C ) STRANDEDNESS: single
( D ) TOPOLOGY: linear (i i) MOLECULE TYPE: cDNA to mRNA (v i) ORIGINAL SOURCE:
    (A) ORGANISM: Homo sapiens (v i i) IMMEDIATE SOURCE:
    (B) CLONE: EBHC202 primer (x i) SEQUENCE DESCRIPTION: SEQ ID NO: 9:

GCGGATCCGC AGCAAAAGCC CTCATAGCTT T    31

(2) INFORMATION FOR SEQ ID NO: 10:

(i) SEQUENCE CHARACTERISTICS:
        (A) LENGTH: 29 bases
        (B) TYPE: nucleic acid
        (C) STRANDEDNESS: single
        (D) TOPOLOGY: linear (i i) MOLECULE TYPE: cDNA to mRNA (v i) ORIGINAL SOURCE:
        (A) ORGANISM: Homo sapiens (v i i) IMMEDIATE SOURCE:
        (B) CLONE: EBHC204 primer (x i) SEQUENCE DESCRIPTION: SEQ ID NO: 10:

GCGGATCCTC TAGCAATCAC CTGAGTGCC    29

(2) INFORMATION FOR SEQ ID NO: 11:

(i) SEQUENCE CHARACTERISTICS:
        (A) LENGTH: 24 bases
        (B) TYPE: nucleic acid
        (C) STRANDEDNESS: single
        (D) TOPOLOGY: linear (i i) MOLECULE TYPE: cDNA to mRNA (v i) ORIGINAL SOURCE:
        (A) ORGANISM: Homo sapiens (v i i) IMMEDIATE SOURCE:
        (B) CLONE: lambda gt11 forward primer (x i) SEQUENCE DESCRIPTION: SEQ ID NO: 11:

GGTGGCGACG ACTCCTGGAG CCCG    24

(2) INFORMATION FOR SEQ ID NO: 12:

(i) SEQUENCE CHARACTERISTICS:
        (A) LENGTH: 24 bases
        (B) TYPE: nucleic acid
        (C) STRANDEDNESS: single
        (D) TOPOLOGY: linear (i i) MOLECULE TYPE: cDNA to mRNA (v i) ORIGINAL SOURCE:
        (A) ORGANISM: Homo sapiens (v i i) IMMEDIATE SOURCE:
        (B) CLONE: lambda gt11 reverse primer (x i) SEQUENCE DESCRIPTION: SEQ ID NO: 12:

TTGACACCAG ACCAACTGGT AATG    24

(2) INFORMATION FOR SEQ ID NO: 13:

(i) SEQUENCE CHARACTERISTICS:

( A ) LENGTH: 28 bases
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC211 primer ( x i ) SEQUENCE DESCRIPTION: SEQ ID NO: 13:

AGCGGATCCA GTGTTTAGCT TCCCCACG 28

( 2 ) INFORMATION FOR SEQ ID NO: 14:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC219 primer ( x i ) SEQUENCE DESCRIPTION: SEQ ID NO: 14:

AGCGGATCCT CAACGATGGA AAGGAACATG 30

( 2 ) INFORMATION FOR SEQ ID NO: 15:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Homo sapiens ( v i i ) IMMEDIATE SOURCE:
( B ) CLONE: EBHC215 primer ( x i ) SEQUENCE DESCRIPTION: SEQ ID NO: 15:

AGCGGATCCA GGAACACTTA ATCATTTGG C 31

( 2 ) INFORMATION FOR SEQ ID NO: 16:

( i ) SEQUENCE CHARACTERISTICS:
( A ) LENGTH: 19 amino acids
( B ) TYPE:AMINO
( B ) TYPE:AMINO
( C ) STRANDEDNESS: single
( D ) TOPOLOGY: linear ( i i ) MOLECULE TYPE: peptide ( v i ) ORIGINAL SOURCE:
( A ) ORGANISM: Homo sapiens ( v i i ) IMMEDIATE SOURCE:
( B ) CLONE: muc2 acceptor peptide ( x i ) SEQUENCE DESCRIPTION: SEQ ID NO: 16:

Pro Thr Thr Pro Ile Ser Thr Thr Thr Met Val Thr Pro Thr Pro Thr

Pro Thr Cys (2) INFORMATION FOR SEQ ID NO: 17:

(i) SEQUENCE CHARACTERISTICS:
        (A) LENGTH: 20 amino acids
        (B) TYPE:AMINO
        (B) TYPE:AMINO
        (C) STRANDEDNESS: single
        (D) TOPOLOGY: linear (ii) MOLECULE TYPE: peptide (vi) ORIGINAL SOURCE:
        (A) ORGANISM: Homo sapiens (vii) IMMEDIATE SOURCE:
        (B) CLONE: muc5C acceptor peptide (xi) SEQUENCE DESCRIPTION: SEQ ID NO: 17:

Cys Thr Thr Ser Thr Thr Ser Ala Pro Thr Ser Thr Thr Ser Ala
                5                    10                    15
Pro Thr Thr Ser (2) INFORMATION FOR SEQ ID NO: 18:

(i) SEQUENCE CHARACTERISTICS:
        (A) LENGTH: 21 amino acids
        (B) TYPE:AMINO
        (B) TYPE:AMINO
        (C) STRANDEDNESS: single
        (D) TOPOLOGY: linear (ii) MOLECULE TYPE: peptide (vi) ORIGINAL SOURCE:
        (A) ORGANISM: Homo sapiens (vii) IMMEDIATE SOURCE:
        (B) CLONE: HIV-V3 acceptor peptide (xi) SEQUENCE DESCRIPTION: SEQ ID NO: 18:

Cys Ile Arg Ile Gln Arg Gly Pro Gly Arg Ala Phe Val Thr Ile Gly
                5                    10                    15
Lys Ile Gly Asn Met
            20

(2) INFORMATION FOR SEQ ID NO: 19:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens (vii) IMMEDIATE SOURCE:
        (B) CLONE: EBHC249 primer (xi) SEQUENCE DESCRIPTION: SEQ ID NO: 19:

AGCGGATCCT GAATAGCTAC TAATACCATC G                31